(12) United States Patent
Miyamoto et al.

(10) Patent No.: US 7,759,437 B2
(45) Date of Patent: Jul. 20, 2010

(54) NORBORNENE DERIVATIVE, NORBORNENE POLYMER PRODUCED BY RING-OPENING (CO)POLYMERIZATION, AND PROCESS FOR PRODUCING THE POLYMER BY RING-OPENING (CO)POLYMERIZATION

(75) Inventors: Yoshikazu Miyamoto, Tokyo (JP); Nobuyuki Miyaki, Tokyo (JP); Kohei Goto, Tokyo (JP); Yuichi Hashiguchi, Tokyo (JP)

(73) Assignee: JSR Corporation, Tokyo (JP)

( * ) Notice: Subject to any disclaimer, the term of this patent is extended or adjusted under 35 U.S.C. 154(b) by 0 days.

(21) Appl. No.: 12/416,451

(22) Filed: Apr. 1, 2009

(65) Prior Publication Data
US 2009/0247798 A1    Oct. 1, 2009

Related U.S. Application Data

(62) Division of application No. 10/556,717, filed as application No. PCT/JP2004/006095 on Apr. 27, 2004, now Pat. No. 7,541,411.

(30) Foreign Application Priority Data

| May 14, 2003 | (JP) | ............................. 2003-135702 |
| Jun. 27, 2003 | (JP) | ............................. 2003-185203 |

(51) Int. Cl.
*C08G 61/00* (2006.01)
*C08G 61/06* (2006.01)
*C07C 1/00* (2006.01)
*C07C 13/00* (2006.01)
*C07C 13/72* (2006.01)
*C07C 25/24* (2006.01)
*C07C 43/215* (2006.01)
*C07C 43/285* (2006.01)

(52) U.S. Cl. .................................. 525/539; 430/270.1
(58) Field of Classification Search ................. 525/539; 430/270.1
See application file for complete search history.

(56) References Cited

U.S. PATENT DOCUMENTS

| 5,334,424 A | 8/1994 | Hani et al. |
| 7,541,411 B2 * | 6/2009 | Miyamoto et al. .......... 525/539 |

FOREIGN PATENT DOCUMENTS

| EP | 0 591 536 | 4/1994 |
| JP | 1-240517 | 9/1989 |
| JP | 4-245202 | 9/1992 |
| JP | 5-2108 | 1/1993 |
| JP | 5-61026 | 3/1993 |
| JP | 5-64865 | 3/1993 |
| JP | 5-212828 | 8/1993 |
| JP | 7-77608 | 3/1995 |
| WO | WO 01/60811 | 8/2001 |

OTHER PUBLICATIONS

Nelson et al., J. Org. Chem., vol. 40, No. 25, pp. 3658-3664, 1975.
Nagao et al., Tetrahedron, vol. 40, No. 8, pp. 1215-1223, 1984.
Ohwada, J. Am. Chem. Soc., vol. 114, pp. 8818-8827, 992.
Jason et al., J. Org. Chem., vol. 56, pp. 3664-3669, 1991.

* cited by examiner

*Primary Examiner*—Duc Truong
(74) *Attorney, Agent, or Firm*—Oblon, Spivak, McClelland, Maier & Neustadt, L.L.P.

(57) ABSTRACT

The norbornene derivative of the present invention is represented by the following formula (Im).

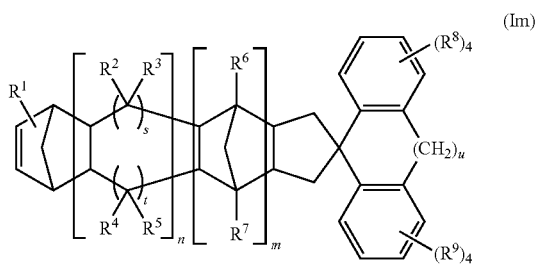

According to the present invention, a novel norbornene derivative that is useful as a precursor monomer for preparing a cycloolefin polymer exhibiting excellent transparency, heat resistance and low-water absorption properties and having been freely controlled in the birefringence properties and the wavelength dispersion properties can be provided. According to the present invention, further, a norbornene ring-opened (co)polymer having excellent transparency and heat resistance, exhibiting high solubility in organic solvents and having specific birefringence properties and wavelength dependence, and a process for preparing the ring-opened (co)polymer can be provided.

11 Claims, 8 Drawing Sheets

FIG. 3

NORBORNENE DERIVATIVE, NORBORNENE POLYMER PRODUCED BY RING-OPENING (CO)POLYMERIZATION, AND PROCESS FOR PRODUCING THE POLYMER BY RING-OPENING (CO)POLYMERIZATION

CROSS REFERENCE TO RELATED APPLICATION

This application is a divisional application of U.S. application Ser. No. 10/556,717, filed on Nov. 14, 2005, now U.S. Pat. No. 7,541,411 which is a 371 of PCT/JP04/006095, filed on Apr. 27, 2004, and claims priority to the following applications: Japanese Patent Application No. 2003-135702, filed on May 14, 2003, and Japanese Patent Application No. 2003-185203, filed on Jun. 27, 2003.

TECHNICAL FIELD

The present invention relates to a novel norbornene derivative. More particularly, the invention relates to a novel norbornene derivative that is favorably used as a precursor monomer for preparing a cycloolefin polymer having excellent transparency, heat resistance and low-water absorption properties and capable of being freely controlled in the magnitude of birefringence and the wavelength dispersion properties.

The present invention also relates to a nornornene ring-opened (co)polymer having structural units derived from the above-mentioned norbornene derivative and a process for preparing the ring-opened (co)polymer. More particularly, the invention relates to a norbornene ring-opened (co)polymer having excellent transparency and heat resistance, exhibiting high solubility in organic solvents and having specific birefringence properties and wavelength dependence, and a process for preparing the ring-opened (co) polymer.

BACKGROUND ART

Since cycloolefin resins produced using cycloolefins as monomers have a bulky alicyclic structure in the main chain skeleton, they are amorphous and have excellent transparency, heat resistance, small coefficient of photoelasticity, and properties of low-water absorption, acid resistance, alkali resistance and high electrical insulation, etc. On this account, uses of cycloolefin polymers for displays (retardation films, diffusion films, liquid crystal substrates, films for touch panels, light guide plates, polarizing plate protective films), optical lenses, optical discs (CD, MD, CD-R, DVD, etc.), optical fibers, optical films/sheets, sealing of photosemiconductors, etc. have been studied.

Of such cycloolefin resins, cycloolefin resins using norbornenes of particularly high reactivity as precursors have been mainly developed, and with remarkable growth of optoelectronics technology, the demand for them has been increased.

As described above, utilization of the films made of the cycloolefin resins as polarizing plate protective films or liquid crystal substrate materials has been expected because the films have relatively small birefringence, and utilization of the films as optical compensation films such as retardation films has been expected because the films have phase difference stability.

For example, in Japanese Patent Laid-Open Publication No. 245202/1992, Japanese Patent Laid-Open Publication No. 36120/1992, Japanese Patent Laid-Open Publication No. 2108/1993 and Japanese Patent Laid-Open Publication No. 64865/1993, phase plates using films of cycloolefin resins are described. In Japanese Patent Laid-Open Publication No. 212828/1993 and Japanese Patent Laid-Open Publication No. 77608/1995, uses of films of cycloolefin resins as protective films for polarizing plates are described. In Japanese Patent Laid-Open Publication No. 61026/1993, a substrate for a liquid crystal display element comprising a film of a cycloolefin resin is described.

On the other hand, liquid crystal displays, practical use of which started with electronic calculators, digital clocks, audio displays, etc., came to be applied to various equipments, such as various mobile equipments (notebook PC, PDA, cellular phones), liquid crystal television sets, car navigation systems and various liquid crystal monitors, making the best use of their features of extremely small thickness, compact size and low power consumption. In the mobile equipments, further, functions of e-mailing and access to information sites are regarded as important because of recent acceleration of the information-oriented age, and for the displays, coloration or much higher precision are desired. Under such circumstances, special characteristics such as capability of being freely controlled in the optical properties have been required for the materials used.

For example, in order to attain high functions and low power consumption, a semi-transmission type display system imparted with a reflection function and a transmission function has been paid attention in the mobile liquid crystal cells of recent years. For the semi-transmission type display system, materials having wavelength dispersion (reciprocal wavelength dispersion properties) such that the phase difference becomes greater toward a longer wavelength side (upward to the right) are required to obtain a circularly polarized light in a wide wavelength region. Retardation films, however, are generally imparted with a function to give phase difference (birefringence) to a transmitted light by stretching and orientation, and as the wavelength of a transmitted light becomes longer, the absolute value of phase difference (birefringence) of the transmitted light tends to become smaller. Therefore, it is very difficult to give specific phase difference, e.g., that of ¼ wavelength, to a transmitted light in the whole visible region (400 to 800 nm), and in case of the conventional cycloolefin resins, it has not been attained so far to allow one film to exhibit such optical properties of high level.

At present, however, retardation films that give phase difference of ¼ wavelength in the whole visible region (400 to 800 nm) are actually required for the reflection type or semi-transmission type liquid crystal displays or the pickups for optical discs, and moreover, for the liquid crystal projectors, phase difference of ½λ is required.

In case of optical films made of the conventional cycloolefin resins, therefore, two or more films need to be laminated to attain such phase differences. In the production of optical films constituted of laminated films, however, there is a problem that a complicated process including laminating, cutting and bonding of films must be carried out because the two films need to be laminated at precise angles, and hence, productivity becomes extremely bad. Further, there is another problem that the resulting retardation film becomes thick, and this hinders weight lightening or downsizing when they are applied to mobile equipments.

Under the circumstances where downsizing and weight lightening of mobile equipments, are promoted as described above, actualization of single-layer optical films having desired phase difference in a wide wavelength region is desired, and development of cycloolefin resins capable of being freely controlled in the magnitude of birefringence and the wavelength dispersion properties according to the properties required in the optical field is eagerly desired.

In the light of such circumstances as mentioned above, the present inventor have earnestly studied, and as a result, they have found that a novel norbornene ring-opened (co)polymer obtained from a specific novel norbornene derivative and a hydrogenation product of the ring-opened (co)polymer can be controlled not only in the magnitude of birefringence (phase difference) but also in the wavelength dependence by designing polymerization composition and substituents of a monomer. Based on the finding, the present invention has been accomplished.

It is an object of the present invention to provide a novel norbornene derivative that is employable as a precursor of a cycloolefin polymer exhibiting excellent transparency, heat resistance and low-water absorption properties and having birefringence and wavelength dispersion properties having been controlled to a desired extent.

It is another object of the present invention to provide a novel norbornene ring-opened (co)polymer capable of producing optical materials having desired birefringence properties and wavelength dependence and having excellent transparency and heat resistance, and a process for preparing the ring-opened (co)polymer.

DISCLOSURE OF THE INVENTION

The norbornene derivative of the present invention is represented by the following formula (Im):

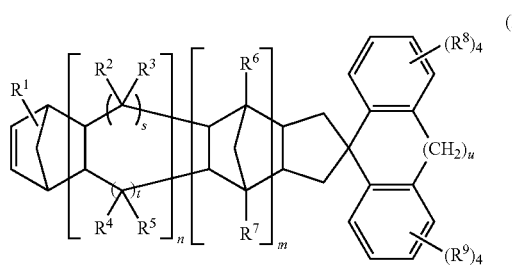

(Im)

wherein $R^1$, $R^2$, $R^3$, $R^4$, $R^5$, $R^6$, $R^7$, $R^8$ and $R^9$ are each independently an atom or a group selected from the group consisting of a hydrogen atom, a halogen atom, a substituted or unsubstituted hydrocarbon group of 1 to 30 carbon atoms which may have a linkage containing an oxygen atom, a nitrogen atom, a sulfur atom or a silicon atom, and a polar group, s, t and u are each independently an integer of 0 to 3, and m and n are each independently an integer of 0 to 2.

In the norbornene derivative of the invention, it is preferable that in the formula (Im), n is 0 and m is 0 or 1, and it is preferable that in the formula (Im), u is 0 or 1.

In the norbornene derivative of the invention, it is also preferable that in the formula (Im), n is 1 or 2, s and t are each 1, and u is 0 or 1. In the norbornene derivative of the invention, it is preferable that in the formula (Im), 3 or more of $R^8$ and 3 or more of $R^9$ are each a hydrogen atom.

The norbornene ring-opened (co)polymer of the present invention has structural units (I) represented by the following formula (I):

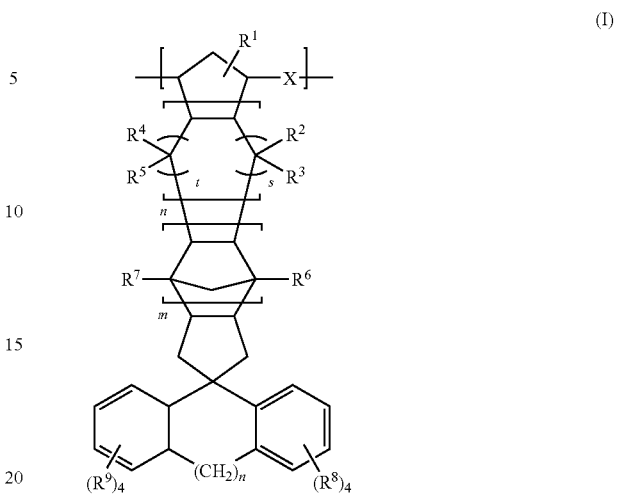

(I)

wherein m and n are each independently an integer of 0 to 2,

X is a group represented by the formula —CH=CH— or a group represented by the formula —CH$_2$CH$_2$—, $R^1$, $R^2$, $R^3$, $R^4$, $R^5$, $R^6$, $R^7$, $R^8$ and $R^9$ are each independently an atom or a group selected from the group consisting of a hydrogen atom, a halogen atom, a substituted or unsubstituted hydrocarbon group of 1 to 30 carbon atoms which may have a linkage containing an oxygen atom, a nitrogen atom, a sulfur atom or a silicon atom, and a polar group, and s, t and u are each independently an integer of 0 to 3.

In the norbornene ring-opened (co)polymer of the invention, the structural units (I) are preferably contained in amounts of not less than 2% by mol of all structural units.

The norbornene ring-opened (co)polymer of the invention preferably further has structural units (II) represented by the following formula (II):

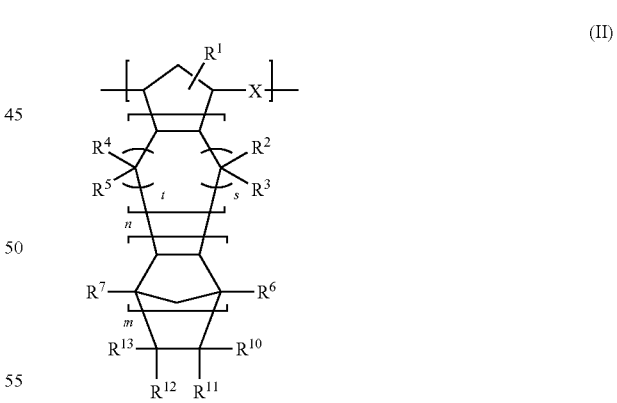

(II)

wherein m and n are each independently an integer of 0 to 2,

X is a group represented by the formula —CH=CH— or a group represented by the formula —CH$_2$CH$_2$—, $R^1$, $R^2$, $R^3$, $R^4$, $R^5$, $R^6$ and $R^7$ are each independently an atom or a group selected from the group consisting of a hydrogen atom, a halogen atom, a substituted or unsubstituted hydrocarbon group of 1 to 30 carbon atoms which may have a linkage containing an oxygen atom, a nitrogen atom, a sulfur atom or a silicon atom, and a polar group, $R^{10}$, $R^{11}$, $R^{12}$ and $R^{13}$ are each independently an atom or a group selected from the group consisting of a hydrogen atom, a halogen atom, a substituted or unsubstituted hydrocarbon group of 1 to 30 carbon atoms which may have a linkage containing an oxygen atom, a nitrogen atom, a sulfur atom or a silicon atom, and a polar group, they may be bonded to each other to form a monocyclic or polycyclic group which may have a hetero atom, and $R^{10}$ and $R^{11}$, or $R^{12}$ and $R^{13}$ may be united to form a divalent hydrocarbon group, and s and t are each independently an integer of 0 to 3.

In the norbornene ring-opened (co)polymer of the invention, the structural units (II) are preferably contained in amounts of not more than 98% by mol of all structural units.

In the norbornene ring-opened (co)polymer of the invention, the total amount of the structural units (I) and the structural units (II) is preferably not less than 5% by mol of all structural units.

In the norbornene ring-opened (co)polymer of the invention, it is preferable that X in an amount of not less than 90% by mol of the total amount of X in the structural units (I) and the structural units (II) is a group represented by —$CH_2CH_2$—.

In the norbornene ring-opened (co)polymer of the invention, the structural unite (I) are preferably structural units of the formula (I) in which m is 0, n is 0, and u is 0.

The process for preparing a norbornene ring-opened (co) polymer of the present invention comprises ring-opening (co) polymerizing a norbornene monomer (Im) represented by the following formula (Im) optionally together with a norbornene monomer (IIm) represented by the following formula (IIm);

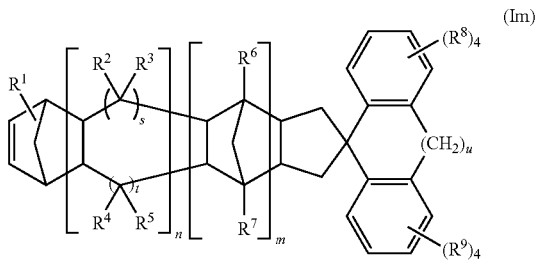

(Im)

wherein m and n are each independently an integer of 0 to 2, $R^1$, $R^2$, $R^3$, $R^4$, $R^5$, $R^6$, $R^7$, $R^8$ and $R^9$ are each independently an atom or a group selected from the group consisting of a hydrogen atom, a halogen atom, a substituted or unsubstituted hydrocarbon group of 1 to 30 carbon atoms which may have a linkage containing an oxygen atom, a nitrogen atom, a sulfur atom or a silicon atom, and a polar group, and s, t and u are each independently an integer of 0 to 3;

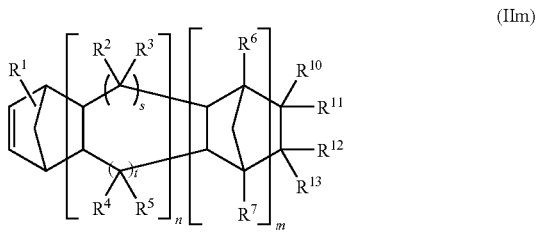

(IIm)

wherein m and n are each independently an integer of 0 to 2, $R^1$, $R^2$, $R^3$, $R^4$, $R^5$, $R^6$ and $R^7$ are each independently an atom or a group selected from the group consisting of a hydrogen atom, a halogen atom, a substituted or unsubstituted hydrocarbon group of 1 to 30 carbon atoms which may have a linkage containing an oxygen atom, a nitrogen atom, a sulfur atom or a silicon atom, and a polar group, $R^{10}$, $R^{11}$, $R^{12}$ and $R^{13}$ are each independently an atom or a group selected from the group consisting of a hydrogen atom, a halogen atom, a substituted or unsubstituted hydrocarbon group of 1 to 30 carbon atoms which may have a linkage containing an oxygen atom, a nitrogen atom, a sulfur atom or a silicon atom, and a polar group, they may be bonded to each other to form a monocyclic or polycyclic group which may have a hetero atom, and $R^{10}$ and $R^{11}$, or $R^{12}$ and $R^{13}$ may be united to form a divalent hydrocarbon group, and s and t are each independently an integer of 0 to 3.

The process for preparing a norbornene ring-opened (co) polymer of the invention preferably comprises ring-opening (co)polymerizing the norbornene monomer (Im) represented by the formula (Im) optionally together with the norbornene monomer (IIm) represented by the formula (IIm) and then hydrogenating the resulting (co)polymer.

The present invention declares the right of priority from Japanese Patent Application No. 135702/2003 and Japanese Patent Application No. 185207/2003 and claims them by citing them.

BRIEF DESCRIPTION OF THE DRAWINGS

FIG. 3 shows a $^1$H-NMR spectrum of a norbornene derivative obtained in Example 2.

BEST MODE FOR CARRYING OUT THE INVENTION

Figure 1:
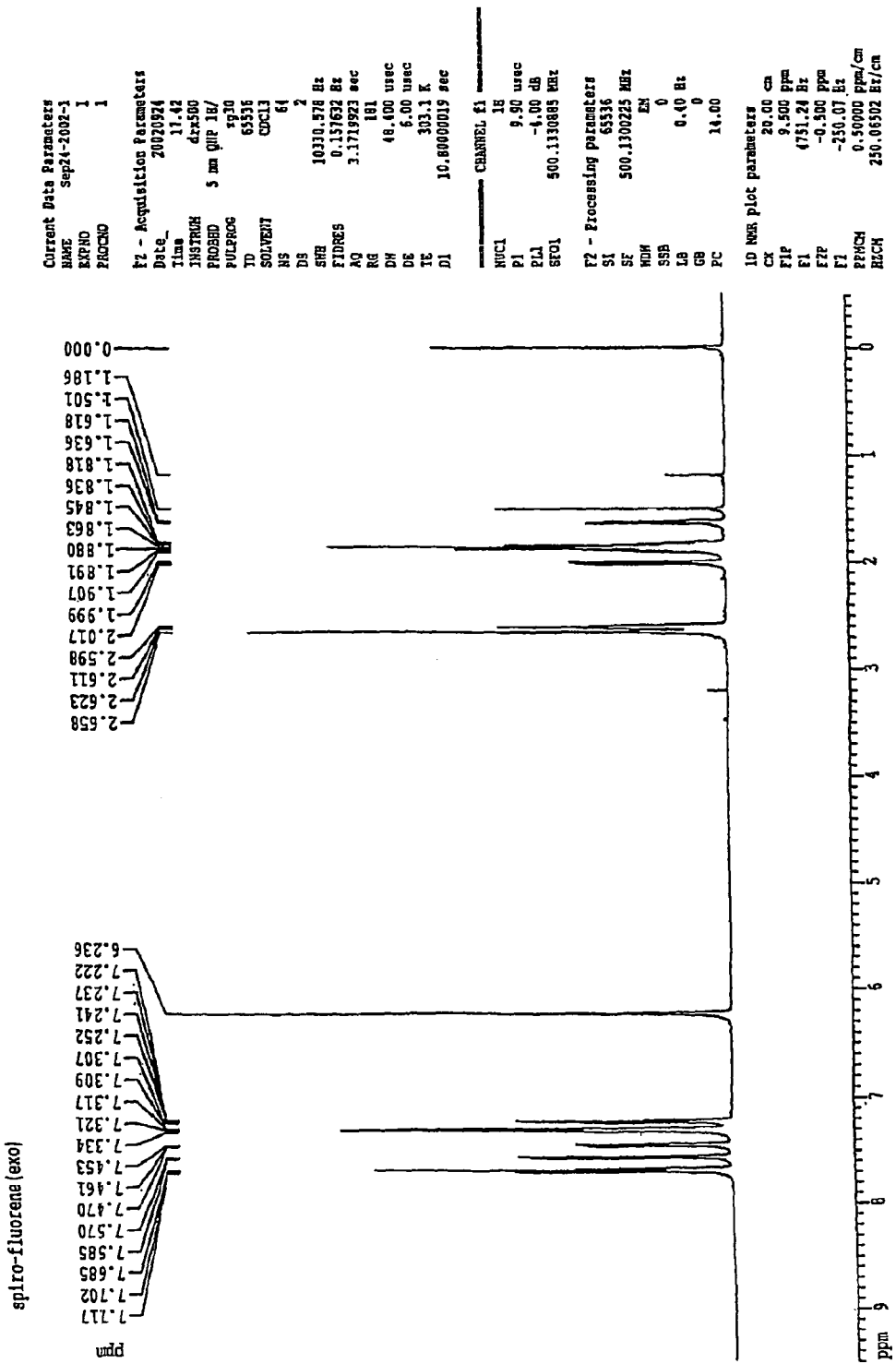
FIG. 1 shows a $^1$H-NMR spectrum of a norbornene derivative obtained in Example 1.

The present invention is described in detail hereinafter.

Norbornene Derivative

The norbornene derivative of the invention is represented by the following formula (Im).

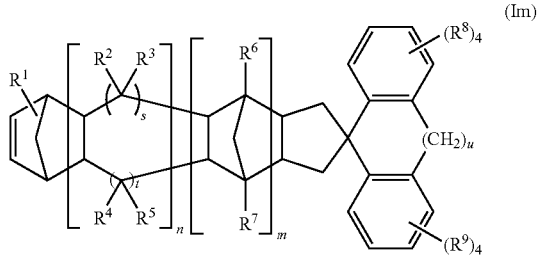

(Im)

In the formula (Im), $R^1$, $R^2$, $R^3$, $R^4$, $R^5$, $R^6$, $R^7$, $R^8$ and $R^9$ are each independently an atom or a group selected from the group consisting of a hydrogen atom, a halogen atom, a substituted or unsubstituted hydrocarbon group of 1 to 30 carbon atoms which may have a linkage containing an oxygen atom, a nitrogen atom, a sulfur atom or a silicon atom, and a polar group.

Examples of the halogen atoms include a fluorine atom, a chlorine atom and a bromine atom.

Examples of the hydrocarbon groups of 1 to 30 carbon atoms include alkyl groups, such as methyl, ethyl and propyl; cycloalkyl groups, such as cyclopentyl and cyclohexyl; alkenyl groups, such as vinyl and allyl; alkylidene groups, such as ethylidene and propylidene; and aromatic groups, such as phenyl, naphthyl and anthracenyl. These hydrocarbon groups may be substituted, and examples of substituents include halogen atoms, such as fluorine, chlorine and bromine, a phenylsulfonyl group and a cyano group.

The substituted or unsubstituted hydrocarbon group may be directly bonded to a ring structure or may be bonded thereto through a linkage. Examples of the linkages include divalent hydrocarbon groups of 1 to 10 carbon atoms (e.g., alkylene group represented by $—(CH_2)_q—$ wherein q is an integer of 1 to 10), linkages containing an oxygen atom, a nitrogen atom, a sulfur atom or a silicon atom (e.g., carbonyl group (—CO—), carbonyloxy group (—COO—), sulfonyl group (—SO$_2$—), sulfonyl ester group (—SO$_2$—O—), ether bond (—O—), thioether bond (—S—), imino group (—NH—), amide bond (—NHCO—), siloxane bond (—Si(R$_2$)O— wherein R is an alkyl group such as methyl or ethyl), and combinations of two or more of these groups and linkages.

Examples of the polar groups include a hydroxyl group, an alkoxy group of 1 to 10 carbon atoms, a carbonyloxy group, an alkoxycarbonyl group, an aryloxycarbonyl group, a cyano group, an amide group, an imide group, a triorganosiloxy group, a triorganosilyl group, an amino group, an acyl group, an alkoxysilyl group, a sulfonyl group and a carboxyl group. Examples of the alkoxy groups include methoxy and ethoxy. Examples of the carbonyloxy groups include alkylcarbonyloxy groups, such as acetoxy and propionyloxy; and arylcarbonyloxy groups, such as benzoyloxy. Examples of the alkoxycarbonyl groups include methoxycarbonyl and ethoxycarbonyl. Examples of the aryloxycarbonyl groups include phenoxycarbonyl, naphthyloxycarbonyl, fluorenyloxycarbonyl and biphenylyloxycarbonyl. Examples of the triorganosiloxy groups include trimethylsiloxy and triethylsiloxy. Examples of triorganosilyl groups include trimethylsilyl and triethylsilyl. Examples of the amino groups include a primary amino group. Examples of the alkoxysilyl groups include trimethoxysilyl and triethoxysilyl.

In the formula (Im), s, t and u are each independently an integer of 0 to 3, preferably an integer of 0 to 2, and m and n are each independently an integer of 0 to 2.

If n and m are greater than the above values, purification becomes difficult or lowering of yields takes place, so that preparation of the norbornene derivative sometimes becomes difficult. Moreover, a glass transition temperature (Tg) of a polymer obtained from the norbornene derivative sometimes becomes too high, so that thermal processability such as processability in stretching is lowered.

In the norbornene derivative of the invention, it is preferable that in the formula (Im), n is 0 and m is 0 or 1. In the norbornene derivatives of the invention, it is also preferable that in the formula (Im), u is 0 or 1. In particular, a compound of the formula (Im) wherein m=n=0 and u=0 is preferable because it can be relatively easily synthesized and a polymer obtained by the use of this derivative shows not only an excellent balance between heat resistance and thermal processability but also toughness. Further, a cycloolefin polymer obtained by ring-opening polymerization of the norbornene derivative of the invention wherein m, n and u are the above values has particularly excellent reciprocal wavelength dispersion properties, so that for the purpose of utilizing the reciprocal wavelength dispersion properties, this norbornene derivative is preferable.

When n in the formula (Im) is 1 or 2, preferably 1, it is preferable that s is 1, t is 1, and u is 0 or 1. In particular, a compound wherein n is 1, m is 0 or 1, s is 1, t is 1, and u is 0 is preferable because a polymer obtained by the use of this derivative shows not only an excellent balance between heat resistance and thermal processability but also toughness.

It is preferable that in the formula (Im), 3 or more of $R^8$ and 3 or more of $R^9$ are hydrogen atoms.

Examples of the norbornene derivatives of the invention include spiro compounds obtained by modifying norbornene dimethanol with appropriate leaving groups (tosyl group, halogen atom, etc.) and then allowing it to react with a fluorene anion.

The norbornene derivative of the invention can be obtained specifically by the following preparation process. Specific examples of the norbornene derivatives of the invention include the following compounds. The norbornene derivative of the invention is not particularly limited by the preparation process or to the following examples.

Process for Preparing Norbornene Derivative

The norbornene derivative of the invention is, for example, a spiro compound synthesized by modifying norbornene dimethanol, which is obtained by reducing 5-norbornene-2,3-dicarboxylic anhydride that is a Diels-Alder reaction product of maleic anhydride with cyclopentadiene, with an appropriate leaving group (tosyl group, halogen atom or the like) and then allowing it to react with a fluorene derivative anion. In the 5-norbornene-2,3-dicarboxylic anhydride, two kinds of isomers of endo form and exo form are present, and these isomeric structures are maintained even in the reduction reaction and the cyclization reaction with the fluorene derivative anion, so that it is feasible to intentionally prepare either of the two kinds of isomers of endo form and exo form as the norbornene derivative of the invention. The 5-norbornene-2,3-dicarboxylic anhydride obtained by the Diels-Alder reaction of maleic anhydride with cyclopentadiene usually has an endo form structure, and by the use of this compound as a starting material, a norbonene derivative of endo form can be synthesized. As disclosed in Kastner, K. F. et al., *J. Mol. Catal.* 15, 47 (1982), the 5-norbornene-2,3-dicarboxylic anhydride can be isomerized to exo form by heating at a high temperature of about 180 to 200° C., and by the use of the anhydride of exo form as a material, a norbornene derivative of exo form can be synthesized.

The 5-norbornene-2,3-dicarboxylic anhydride can be converted into a dicarboxylic anhydride having an arbitrary cyclo structure (referred to as a "cycloolefin dicarboxylic anhydride" hereinafter) by allowing the 5-norbornene-2,3-dicarboxylic anhydride to react with cyclopentadiene or dicyclopentadiene in a closed container under the appropriate temperature conditions. The Diels-Alder reaction is carried out under the temperature conditions of usually 150 to 200° C. From the cycloolefin dicarboxylic anhydride produced by this reaction, a norbonene derivative having an arbitrary cyclo structure can be synthesized in the same manner as described above.

Next, a reduction method of the cycloolefin dicarboxylic anhydride is described. The cycloolefin dicarboxylic anhydride can be reduced to a dimethanol form by the use of various reducing reagents. Examples of the reducing reagents include diisobutylaluminum hydride, lithium aluminum hydride, aluminum hydride, lithium trimethoxyaluminum hydride, sodium aluminum hydride, sodium bis(2-methoxyethoxy)aluminum hydride, sodium boron hydride-anhydrous aluminum chloride type, sodium boron hydride-boron trifluoride type, diborane, and diborane-dimethyl sulfide complex. It is also possible to perform reduction by hydrogenation using a ruthenium catalyst such as Ru/C or Ru₂O₅ and an activated Cu—CrO catalyst. Of the above methods, a method to reduce the anhydride using lithium aluminum hydride in a solvent such as ether or tetrahydrofuran is generally carried out, and working examples of reduction reaction of the 5-norbornene-2,3-dicarboxylic anhydride are disclosed in many literatures Ouch as Nelson, W. L. et al., *J. Org. Chem.* 40, 3658 (1975), and Nagao, Yoshimitsu et al., *Tetrahedron* 40, 8, 1215 (1984).

It is necessary to modify the dimethanol form of the cycloolefin dicarboxylic anhydride with an appropriate leaving group (tosyl group, halogen atom or the like) prior to the reaction with a fluorene derivative anion. The tosyl group can be introduced by allowing the dimethanol form to react with p-toluenesulfonyl chloride in pyridine at a low temperature of not higher than room temperature. Further, by the use of an appropriate halogenating agent (thionyl chloride, phosphorus pentachloride, phosphorus trichloride, phosphorus tribromide, phosphorus oxychloride or the like), a dialcohol form can be converted into a dihalide.

The norbornene derivative of the invention can be synthesized by adding the cycloolefin compound, which has been modified with the above leaving group (tosyl group, halogen atom or the like), to a fluorene derivative anion having been previously formed by the use of an appropriate base. This reaction is preferably carried out at a low temperature, and is carried out in the temperature range of usually −78° C. to room temperature. Example of the bases used for forming the fluorene derivative anion include organic lithium, such as n-butyllithium and phenyllithium, metallic amides, such as soda amide and lithium diisopropylamide, metallic hydroxides, such as sodium hydroxide and potassium hydroxide, and metallic alkoxides, such as sodium methoxide, sodium ethoxide and t-butoxypotassium. In Ohwada, Tomohiko, *J. Am. Chem. Soc.* 114, 23, 8818 (1992), an example of synthesis of a spiro cyclic compound, in which a fluorene anion is formed by the use of n-butyllithium and the fluorene anion is allowed to react with 2,4-dihalobutane to synthesize a spiro cyclic compound, is disclosed, and in Jason, Mark E. at al., *J. Org. Chem.* 56, 11, 3664 (1991), an example of synthesis of a spiro cyclic compound, in which a fluorene anion is formed by the use of t-butoxypotassium and the fluorene anion is allowed to react with 2,4-dibromobutane to synthesize a spiro cyclic compound, is disclosed.

SPECIFIC EXAMPLES OF NORBORNENE DERIVATIVES

Examples of the norbornene derivatives of the invention represented by the formula (Im) include the following compounds.

Examples Of Norbornene Derivatives wherein m=n=0

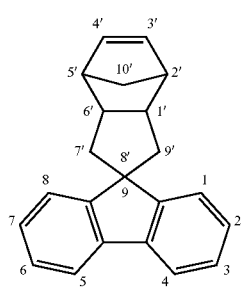

(1) Spiro[fluorene-9,8'-tricyclo[4.3.0.1$^{2,5}$][3]decene]

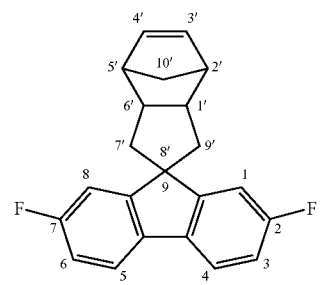

(2) Spiro[2,7-difluorofluorene-9,8'-tricyclo[4.3.0.1$^{2,5}$][3]decene]

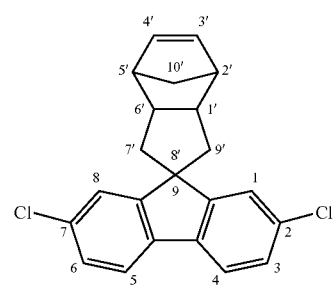

(3) Spiro[2,7-dichlorofluorene-9,8'-tricyclo[4.3.0.1$^{2,5}$][3]decene]

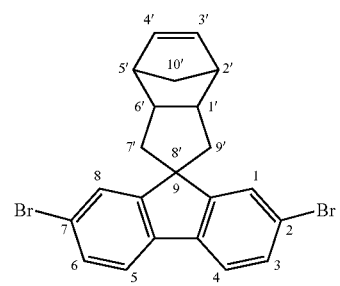

(4) Spiro[2,7-dibromofluorene-9,8'-tricyclo[4.3.0.1$^{2,5}$][3]decene]

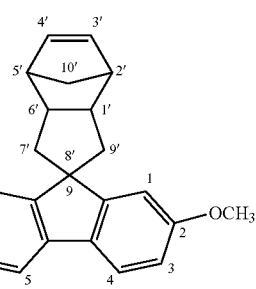

(5) Spiro[2-methoxyfluorene-9,8'-tricyclo[4.3.0.1$^{2,5}$][3]decene]

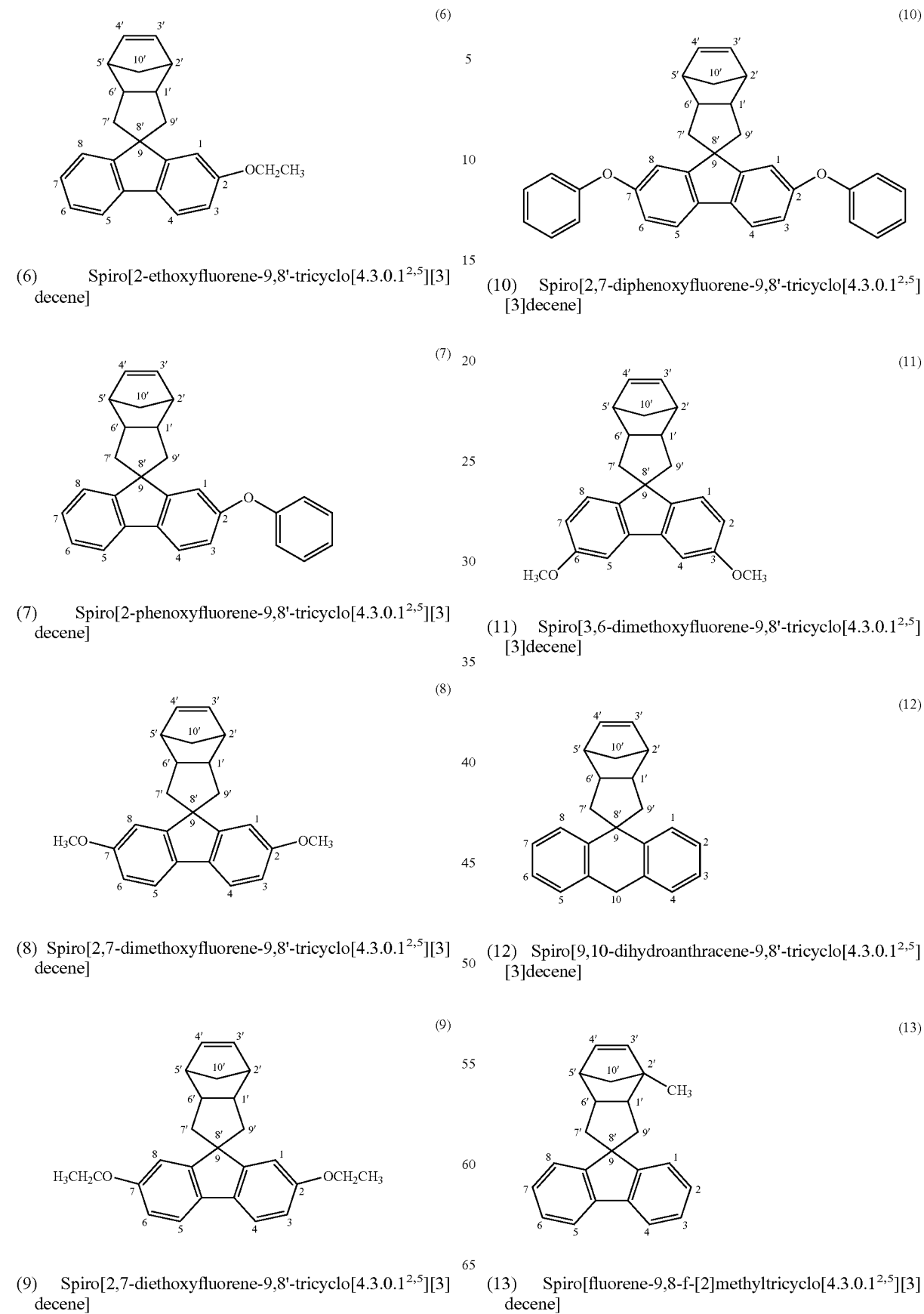

(6) Spiro[2-ethoxyfluorene-9,8'-tricyclo[4.3.0.1$^{2,5}$][3]decene]

(7) Spiro[2-phenoxyfluorene-9,8'-tricyclo[4.3.0.1$^{2,5}$][3]decene]

(8) Spiro[2,7-dimethoxyfluorene-9,8'-tricyclo[4.3.0.1$^{2,5}$][3]decene]

(9) Spiro[2,7-diethoxyfluorene-9,8'-tricyclo[4.3.0.1$^{2,5}$][3]decene]

(10) Spiro[2,7-diphenoxyfluorene-9,8'-tricyclo[4.3.0.1$^{2,5}$][3]decene]

(11) Spiro[3,6-dimethoxyfluorene-9,8'-tricyclo[4.3.0.1$^{2,5}$][3]decene]

(12) Spiro[9,10-dihydroanthracene-9,8'-tricyclo[4.3.0.1$^{2,5}$][3]decene]

(13) Spiro[fluorene-9,8-f-[2]methyltricyclo[4.3.0.1$^{2,5}$][3]decene]

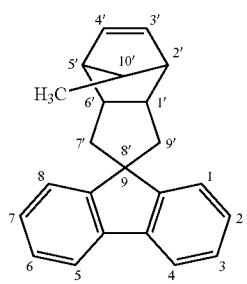

(14) Spiro[fluorene-9,8'-[10]methyltricyclo[4.3.0.1$^{2,5}$][3]decene]

Examples Of Norbornene Derivatives wherein m=1 and n=0

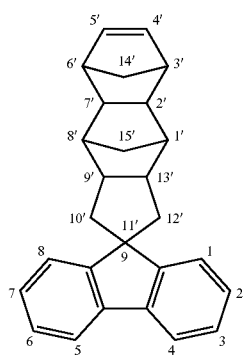

(15) Spiro[fluorene-9,11'-pentacyclo[6.5.1.1$^{3,6}$.0$^{2,7}$.0$^{9,13}$][4]pentadecene]

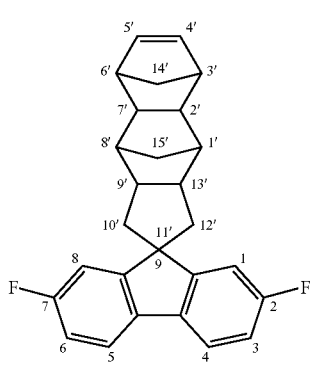

(16) Spiro[2,7-difluorofluorene-9,11'-pentacyclo[6.5.1.1$^{3,6}$.0$^{2,7}$.0$^{9,13}$][4]pentadecene]

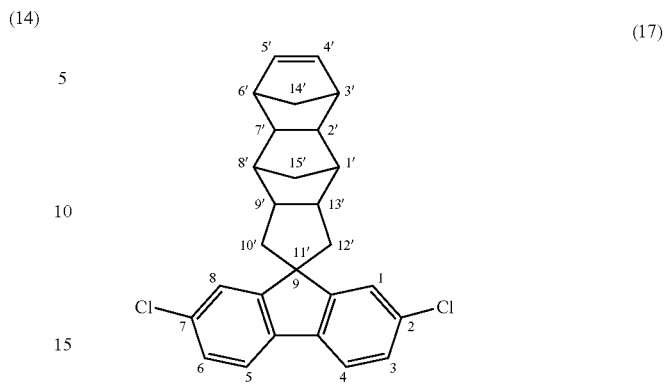

(17) Spiro[2,7-dichlorofluorene-9,11'-pentacyclo[6.5.1.1$^{3,6}$.0$^{2,7}$.0$^{9,13}$][4]pentadecene]

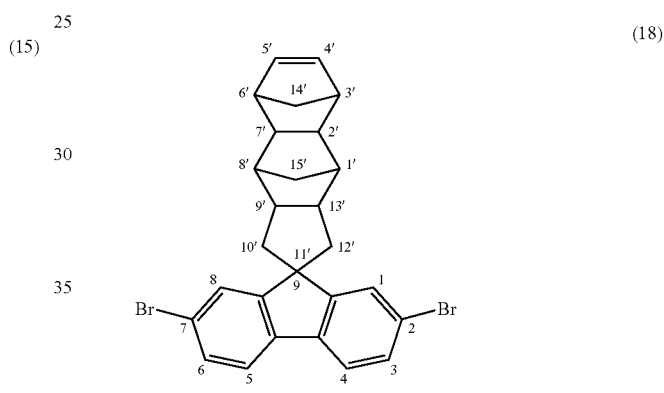

(18) Spiro[2,7-dibromofluorene-9,11'-pentacyclo[6.5.1.1$^{3,6}$.0$^{2,7}$.0$^{9,13}$][4]pentadecene]

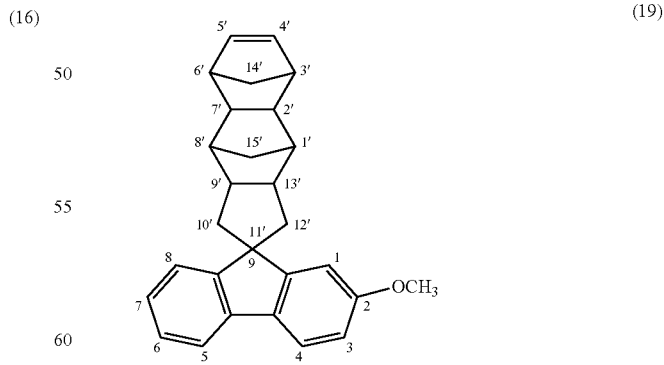

(19) Spiro[2-methoxyfluorene-9,11'-pentacyclo[6.5.1.1$^{3,6}$.0$^{2,7}$.0$^{9,13}$][4]pentadecene]

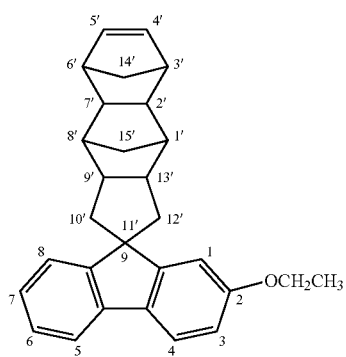

(20) Spiro[2-ethoxyfluorene-9,11'-pentacyclo[6.5.1.1$^{3,6}$.0$^{2,7}$.0$^{9,13}$][4]pentadecene]

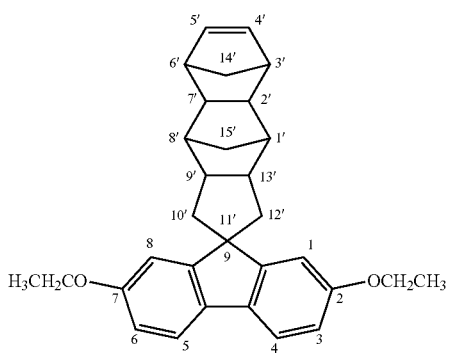

(23) Spiro[2,7-diethoxyfluorene-9,11'-pentacyclo[6.5.1.1$^{3,6}$.0$^{2,7}$.0$^{9,13}$][4]pentadecene]

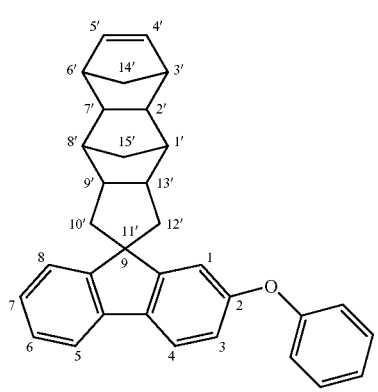

(21) Spiro[2-phenoxyfluorene-5,11'-pentacyclo[6.5.1.1$^{3,6}$.0$^{2,7}$.0$^{9,13}$][4]pentadecene]

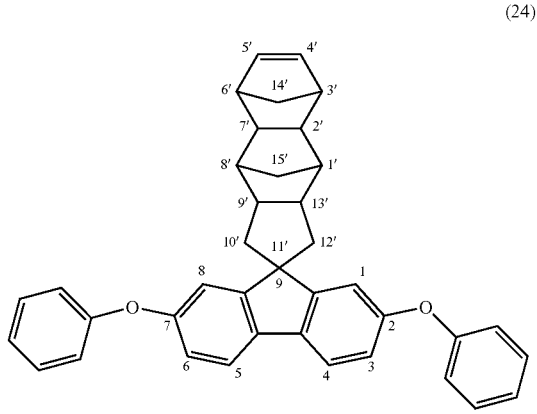

(24) Spiro[2,7-diphenoxyfluorene-9,11'-pentacyclo[6.5.1.1$^{3,6}$.0$^{2,7}$.0$^{9,13}$][4]pentadecene]

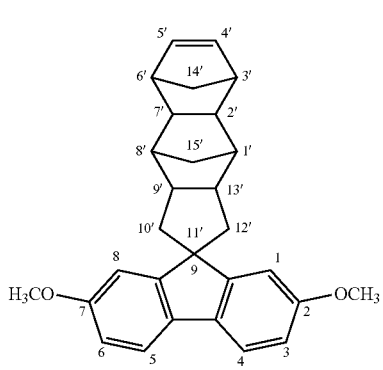

(22) Spiro[2,7-dimethoxyfluorene-9,11'-pentacyclo[6.5.1.1$^{3,6}$.0$^{2,7}$.0$^{9,13}$][4]pentadecene]

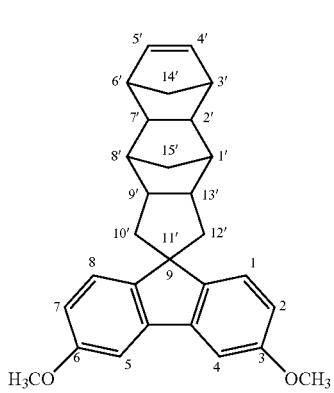

(25) Spiro[3,6-dimethoxyfluorene-9,11'-pentacyclo[6.5.1.1$^{3,6}$.0$^{2,7}$.0$^{9,13}$][4]pentadecene]

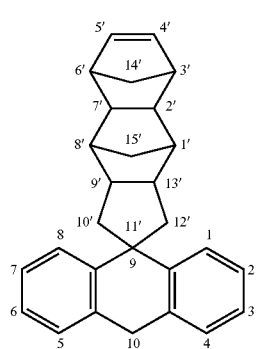

(26) Spiro[9,10-dihydroanthracene-9,11'-pentacyclo[6.5.1.1$^{3,6}$.0$^{2,7}$.0$^{9,13}$][4]pentadecene]

Examples Of Norbornene Derivatives wherein m=1 and n=1

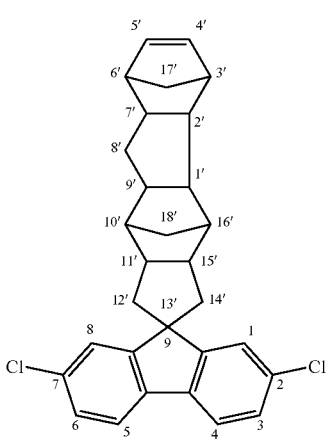

(29) Spiro[2,7-dichlorofluorene-9,13'-hexacyclo[7.7.0.1$^{3,6}$.1$^{10,16}$.0$^{2,7}$.0$^{11,15}$][4]octadecene]

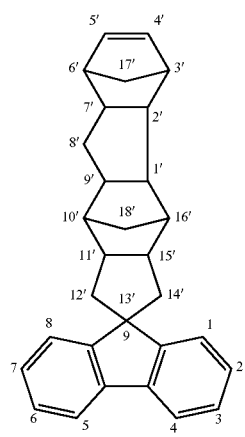

(27) Spiro[fluorene-9,13'-hexacyclo[7.7.0.1$^{3,6}$.1$^{10,16}$.0$^{2,7}$.0$^{11,15}$][4]octadecene]

(30) Spiro[2,7-dibromofluorene-9,13'-hexacyclo[7.7.0.1$^{3,6}$.1$^{10,16}$.0$^{2,7}$.0$^{11,15}$][4]octadecene]

(28) Spiro[2,7-difluorofluorene-9,13'-hexacyclo[7.7.0.1$^{3,6}$.1$^{10,16}$.0$^{2,7}$.0$^{11,15}$][4]octadecene]

(31) Spiro[2-methoxyfluorene-9,13'-hexacyclo[7.7.0.1$^{3,6}$.1$^{10,16}$.0$^{2,7}$.0$^{11,15}$][4]octadecene]

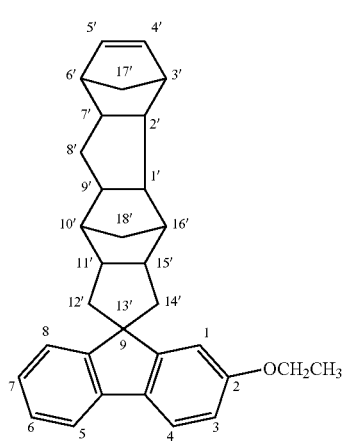

(32) Spiro[2-ethoxyfluorene-9,13'-hexacyclo[7.7.0.1$^{3,6}$.1$^{10,16}$.0$^{2,7}$.0$^{11,15}$][4]octadecene]

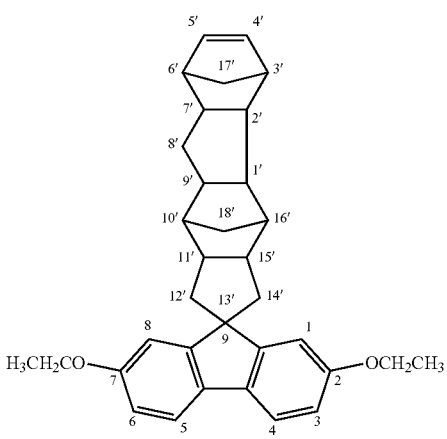

(35) Spiro[2,7-diethoxyfluorene-9,13'-hexacyclo[7.7.0.1$^{3,6}$.1$^{10,16}$.0$^{2,7}$.0$^{11,15}$][4]octadecene]

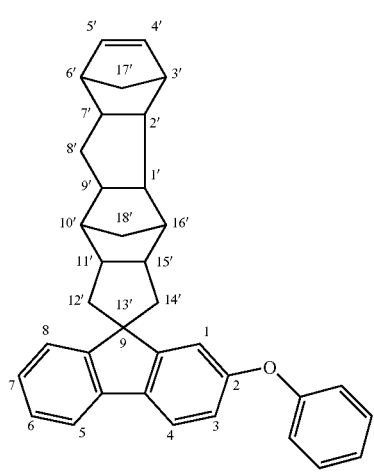

(33) Spiro[2-phenoxyfluorene-9,13'-hexacyclo[7.7.0.1$^{3,6}$.1$^{10,16}$.0$^{2,7}$.0$^{11,15}$][4]octadecene]

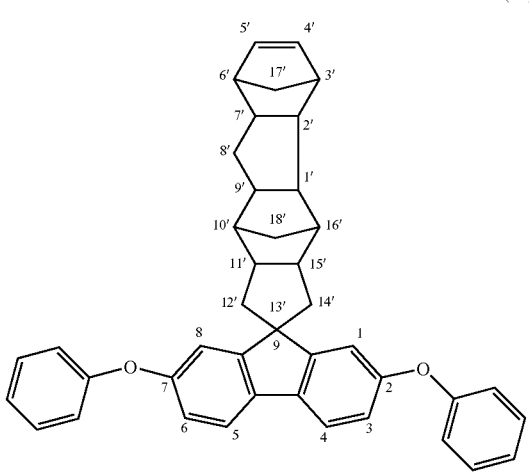

(36) Spiro[2,7-diphenoxyfluorene-9,13'-hexacyclo[7.7.0.1$^{3,6}$.1$^{10,16}$.0$^{2,7}$.0$^{11,15}$][4]octadecene]

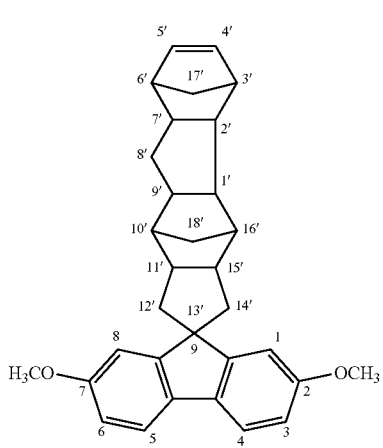

(34) Spiro[2,7-dimethoxyfluorene-9,13'-hexacyclo[7.7.0.1$^{3,6}$.1$^{10,16}$.0$^{2,7}$.0$^{11,15}$][4]octadecene]

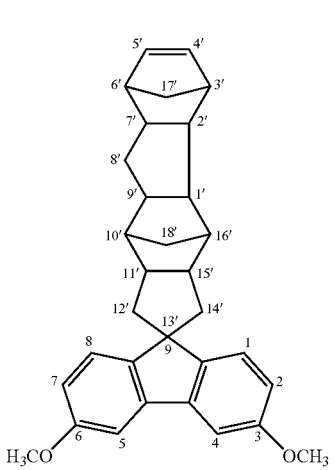

(37) Spiro[3,6-dimethoxyfluorene-9,13'-hexacyclo[7.7.0.1$^{3,6}$.1$^{10,16}$.0$^{2,7}$.0$^{11,15}$][4]octadecene]

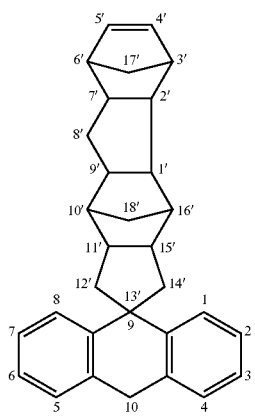

(38)   Spiro[9,10-dihydroanthracene-9,13'-hexacyclo[7.7.0.1$^{3,6}$.0$^{10,16}$.0$^{2,7}$.0$^{11,15}$][4]octadecene]

Examples Of Norbornene Derivatives wherein m=0 and n=1

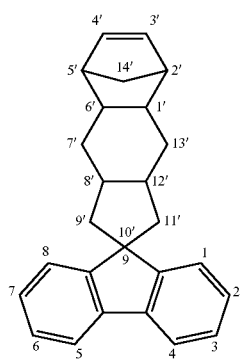

(39)   Spiro[fluorene-9,10'-tetracyclo[7.4.0.0$^{8,12}$.1$^{2,5}$][3]tetradecene]

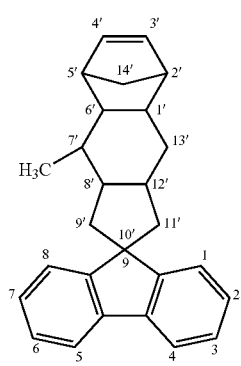

(40)   Spiro[fluorene-9,10'-[7]methyltetracyclo[7.4.0.0$^{8,12}$.1$^{2,5}$][3]tetradecene]

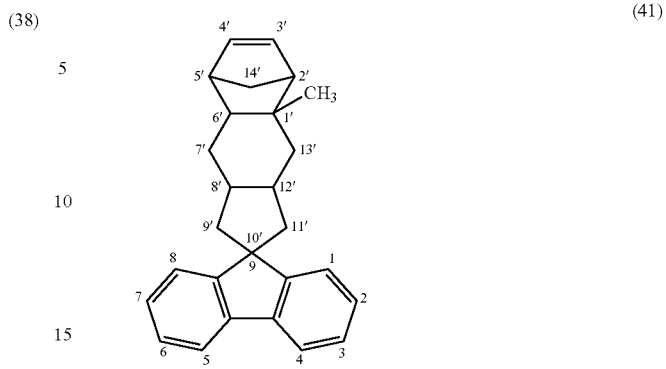

(41)   Spiro[fluorene-9,10'-[1]methyltetracyclo[7.4.0.0$^{8,12}$.1$^{2,5}$][3]tetradecene]

Of the norbornene derivatives of the invention, a compound of the formula (Im) wherein m=n=0, u=0, and 3 or more of R$^8$ and 3 or more of R$^9$ are hydrogen atoms is preferable because it can be relatively easily synthesized and a polymer obtained by the use of this derivative has both of heat resistance and toughness.

The norbornene derivative of the invention can be converted into a desired polymer by ring-opening polymerization, or ring-opening polymerization and the subsequent hydrogenation react-ion, addition polymerization, radical polymerization, cation polymerization, anion polymerization or the like. It is also possible to obtain a copolymer by copolymerization reaction of the norbornene derivative of the invention with an arbitrary copolymerizable compound when needed.

The polymer synthesized from the norbornene derivative of the invention shows excellent transparency, heat resistance and low-water absorption properties and can be arbitrarily controlled in the magnitude of birefringence or the wavelength dispersion properties according to the purpose, so that the polymer can be favorably applied to molding materials of optical discs, photomagnetic discs, optical lenses (Fθ lens, pickup lens, laser printer lens, camera lens, etc.), spectacle lenses, optical films/sheets (display film, retardation film, polarizing film, polarizing plate protective film, diffusion film, anti-reflection film, liquid crystal substrate, EL substrate, substrate for electronic paper, touch panel substrate, PDP front panel, etc.), substrates for transparent conductive films, optical fibers, light guide plates, optical cards, optical mirrors, IC/LSI/LED sealing materials, etc.

Norbornene Ring-opened (Co)Polymer

The norbornene ring-opened (co)polymer of the invention contains structural units (I) represented by the following formula (I) as its essential structural units, and may further contain structural units (II) represented by the following structural formula (II) when needed. In the present invention, the (co)polymer means a polymer or a copolymer. In the present invention, the norbornene ring-opened (co)polymer includes any of a (co)polymer obtained by polymerizing or copolymerizing a norbornene compound and a compound obtained by hydrogenating the (co)polymer.

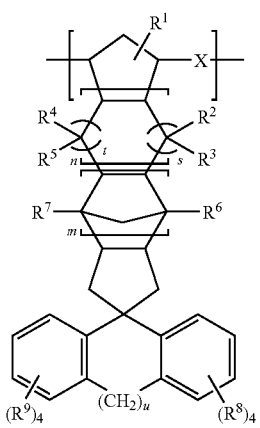

In the formula (I), m and n are each independently an integer of 0 to 2,

X is a group represented by the formula —CH=CH— or a group represented by the formula —CH$_2$CH$_2$—, $R^1$, $R^2$, $R^3$, $R^4$, $R^5$, $R^6$, $R^7$, $R^8$ and $R^9$ are each independently an atom or a group selected from the group consisting of a hydrogen atom, a halogen atom, a substituted or unsubstituted hydrocarbon group of 1 to 30 carbon atoms which may have a linkage containing an oxygen atom, a nitrogen atom, a sulfur atom or a silicon atom, and a polar group, and s, t and u are each independently an integer of 0 to 3.

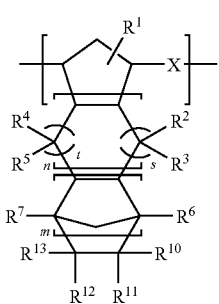

In the formula (II), X, $R^1$, $R^2$, $R^3$, $R^4$, $R^5$, $R^6$, $R^7$, m, n, s and t are the same as those in the formula (I), and $R^{10}$, $R^{11}$, $R^{12}$ and $R^{13}$ are each independently an atom or a group selected from the group consisting of a hydrogen atom, a halogen atom, a substituted or unsubstituted hydrocarbon group of 1 to 30 carbon atoms which may have a linkage containing an oxygen atom, a nitrogen atom, a sulfur atom or a silicon atom, and a polar group, they may be bonded to each other to form a monocyclic or polycyclic group which may have a hetero atom, and $R^{10}$ and $R^{11}$, or $R^{12}$ and $R^{13}$ may be united to form a divalent hydrocarbon group.

As described above, $R^1$ to $R^{13}$ in the formulas (I) and (II) are each independently an atom or a group selected from the group consisting of a hydrogen atom, a halogen atom, a substituted or unsubstituted hydrocarbon group of 1 to 30 carbon atoms which may have a linkage containing an oxygen atom, a nitrogen atom, a sulfur atom or a silicon atom, and a polar group.

Examples of the halogen atoms include a fluorine atom, a chlorine atom and a bromine atom.

Examples of the hydrocarbon groups of 1 to 30 carbon atoms include alkyl groups, such as methyl, ethyl and propyl; cycloalkyl groups, such as cyclopentyl and cyclohexyl; alkenyl groups, such as vinyl and allyl; alkylidene groups, such as ethylidene and propylidene; and aromatic groups, such as phenyl, naphthyl and anthracenyl. These hydrocarbon groups may be substituted, and examples of substituents include halogen atoms, such as fluorine, chlorine and bromine, a phenylsulfonyl group and a cyano group.

The substituted or unsubstituted hydrocarbon group may be directly bonded to a ring structure or may be bonded thereto through a linkage. Examples of the linkages include divalent hydrocarbon groups of 1 to 10 carbon atoms (e.g., alkylene group represented by —(CH$_2$)$_q$— wherein q is an integer of 1 to 10), linkages containing an oxygen atom, a nitrogen atom, a sulfur atom or a silicon atom (e.g., carbonyl group (—CO—), carbonyloxy group (—COO—), sulfonyl group (—SO$_2$—), sulfonyl ester group (—SO$_2$—O—), ether bond (—O—), thioether bond (—S—), imino group (—NH—), amide bond (—NHCO—), siloxane bond (—Si(R$_2$)O— wherein R is an alkyl group such as methyl or ethyl), and combinations of two or more of these groups and linkages.

Examples of the polar groups include a hydroxyl group, an alkoxy group of 1 to 10 carbon atoms, a carbonyloxy group, an alkoxycarbonyl group, an aryloxycarbonyl group, a cyano group, an amide group, an imide group, a triorganosiloxy group, a triorganosilyl group, an amino group, an acyl group, an alkoxysilyl group, a sulfonyl group and a carboxyl group. Examples of the alkoxy groups include methoxy and ethoxy. Examples of the carbonyloxy groups include alkylcarbonyloxy groups, such as acetoxy and propionyloxy; and arylcarbonyloxy groups, such as benzoyloxy. Examples of the alkoxycarbonyl groups include methoxycarbonyl and ethoxycarbonyl. Examples of the aryloxycarbonyl groups include phenoxycarbonyl, naphthyloxycarbonyl, fluorenyloxycarbonyl and biphenylyloxycarbonyl. Examples of the triorganosiloxy groups include trimethylsiloxy and triethylsiloxy. Examples of triorganosilyl groups include trimethylsilyl and triethylsilyl. Examples of the amino groups include a primary amino group. Examples of the alkoxysilyl groups include trimethoxysilyl and triethoxysilyl.

In the formula (I), 4 of 18 and 4 of $R^9$ are each an independent atom or group, and 3 or more of $R^8$ and 3 or more of $R^9$ are preferably hydrogen atoms.

In the formula (II), $R^{10}$, $R^{11}$, $R^{12}$ and $R^{13}$ may be bonded to each other to form a monocyclic or polycyclic group which may have a hetero atom, and $R^{10}$ and $R^{11}$, or $R^{12}$ and $R^{13}$ may be united to form a divalent hydrocarbon group. The structural units (II) represented by the formula (II), however, do not include the structural units (I) represented by the formula (I).

When $R^{10}$, $R^{11}$, $R^{12}$ and $R^{13}$ in the formula (II) are bonded to each other to form a monocyclic or polycyclic group which may have a hetero atom, the monocycle or the polycycle formed may be an aromatic ring or a non-aromatic ring. Examples of the ring structures formed when $R^{10}$, $R^{11}$, $R^{12}$ and $R^{13}$ in the formula (II) are bonded to each other are partially given below.

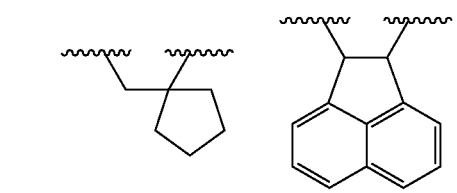

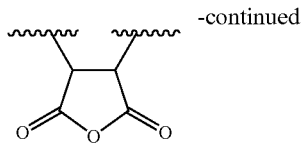
-continued

The structural units (I) to constitute the norbornene ring-opened (co)polymer of the invention are, for example, structural units derived from the later-described monomer (Im) (the aforesaid norbornene derivative represented by the formula (Im)). The structural units (II) contained when needed are, for example, structural units derived from the later-described monomer (IIm).

The norbornene ring-opened (co)polymer of the invention desirably contains the structural units (I) represented by the formula (I) in amounts of usually not less than 2% by mol, preferably not less than 5% by mol, of all structural units.

In the case where the norbornene ring-opened (co)polymer of the invention has the structural units (I) represented by the formula (I) and the structural units (II) represented by the formula (II), the structural units (II) are preferably contained in amounts of not more than 98% by mol of all structural units. In the norbornene ring-opened (co)polymer of the invention, the ratio of the structural units (I) to the structural units (II) (structural units (I)/structural units (II) by mol) is in the range of usually 100/0 to 2/98, preferably 100/0 to 5/95, more preferably 100/0 to 10/90.

The norbornene ring-opened (co)polymer of the invention may further have other structural units in addition to the structural units (I) and the structural units (II). In this case, the norbornene ring-opened (co)polymer of the invention desirably contains the structural units (I) and the structural units (II) in the total amount of preferably not less than 10% by mol, more preferably not less than 15% by mol, of all structural units.

As the structural units other than the structural units (I) and the structural units (II), which may be contained in the norbornene ring-opened (co)polymer of the invention, there can be mentioned structural units derived from monomers copolymerizable with the monomer (Im) (the aforesaid norbornene derivative (Im)) for deriving the structural units (I) and the later-described monomer (IIm) for deriving the structural units (II). Examples of such structural units include those derived from cycloolefins, such as cyclobutene, cyclopentene, cyclooctene and cyclododecene; non-conjugated cyclic polyenes, such as 1,4-cyclooctadiene, dicyclopentadiene and cyclododecatriene; polybutadiene, polyisoprene, polyisoprene, styrene-butadiene, an ethylene/non-conjugated diene polymer, and a low grade polymer having a double bond, such as a non-hydrogenation product of a ring-opened (co)polymer of a norbornene monomer.

In the norbornene ring-opened (co)polymer of the invention, X in an amount of not less than 90% by mol, preferably not less than 95% by mol, more preferably not less than 97% by mol, of the total amount of X in the structural units (I) and the structural units (II) is desirably a group represented by —$CH_2CH_2$—. That is to say, the norbornene ring-opened (co)polymer of the invention is preferably a (co)polymer having been sufficiently hydrogenated and having few double bonds in the main chain. As a proportion of X that is a group represented by —$CH_2$—$CH_2$— to all X in the formula is increased, that is, as the degree of hydrogenation is increased, the norbornene ring-opened (co)polymer of the invention becomes more stable, and coloring or deterioration due to heat can be inhibited, so that higher degree of hydrogenation is preferable.

In the norbornene ring-opened (co)polymer of the invention, the structural units (I) are preferably structural units of the formula (I) wherein m=0, n=0, and u=O. The nornornene ring-opened (co)polymer having such structural units (I) is preferable because it has both of heat resistance and toughness, and besides, a monomer for deriving such structural units can be relatively easily synthesized.

The norbornene ring-opened (co)polymer of the invention desirably has a logarithmic viscosity ($\eta_{inh}$), as measured by an Ubbelohde viscometer, of usually 0.2 to 5.0, preferably 0.3 to 4.0, more preferably 0.35 to 3.0, though the viscosity varies depending upon the purpose. In the molecular weight measurements by gel permeation chromatography (GPC, tetrahydrofuran solvent, in term of polystyrene), the number-average molecular weight (Mn) of the norbornene ring-opened (co)polymer is in the range of usually 1000 to 500000, preferably 2000 to 300000, more preferably 5000 to 300000, and the weight-average molecular weight (Mw) thereof is in the range of usually 5000 to 2000000, preferably 10000 to 1000000, more preferably 10000 to 500000. If the logarithmic viscosity ($\eta_{inh}$) is less than 0.2 and if the number-average molecular weight (Mn) is less than 1000 or the weight-average molecular weight (Mw) is less than 5000, strength of a molded product obtained from the norbornene ring-opened (co)polymer is sometimes markedly lowered, so that such values are undesirable. If the logarithmic viscosity ($\eta_{inh}$) is more than 5.0 and if the number-average molecular weight (Mn) is more than 500000 or the weight-average molecular weight (Mw) is more than 2000000, melt viscosity or solution viscosity of the norbornene ring-opened (co)polymer or its hydrogenation product becomes too high and it becomes difficult to obtain a desired molded article, so that such values are undesirable.

The norbornene ring-opened (co)polymer of the invention and a molded product obtained from the (co)polymer have excellent transparency, heat resistance and low-water absorption properties, and have specific wavelength dependence of birefringence. On this account, by selecting compositional ratios of structural units of the norbornene ring-opened (co)polymer and substituents of the structural units, the norbornene ring-opened (co)polymer of the invention can be used as a material for molded products having desired magnitude of phase difference (birefringence) and desired wavelength dependence.

The norbornene ring-opened (co)polymer of the invention can be used by properly molding it into a desired shape, and can be favorably used particularly for molded articles used in the fields of optical parts and electric or electronic materials. More specifically, the norbornene ring-opened (co)polymer can be used for, for example, optical discs, photomagnetic discs, optical lenses (Fθ lens, pickup lens, laser printer lens, camera lens, etc.), spectacle lenses, optical films (display film, retardation film, polarizing film, transparent conductive film, wave plate, anti-reflection film, optical pickup film, etc.), optical sheets, optical fibers, light guide plates, light diffusion plates, optical cards, optical mirrors, and IC/LSI/LED sealing materials.

To the norbornene ring-opened (co)polymer of the invention, various additives can be added prior to use, when needed. Examples of the additives include phenol or hydroquinone antioxidants, such as 2,6-di-t-butyl-4-methylphenol, 2,2-methylenebis(4-ethyl-6-t-butylphenol), 2,5-di-t-butyl-hydroquinone, pentaerythritoltetrakis[3-(3,5-di-t-butyl-4-hydroxyphenyl)]propionate, 4,4-thiobis-(6-t-butyl-3-methylphenol), 1,1-bis(4-hydroxyphenyl)cyclohexane and octadecyl-3-(3,5-di-t-butyl-4-hydroxyphenyl)propionate; and phosphorus antioxidants, such as tris(4-methoxy-3,5-diphenyl)phosphite, tris(nonylphenyl)phosphite and tris(2,4-di-t-butylphenyl)phosphite. By adding one or more of these antioxidants, oxidation stability of the norbornene ring-opened (co)polymer of the invention can be improved. Further, ultraviolet light absorbers, such as 2,4-dihydroxybenzophenone, 2-hydroxy-4-methoxybenzophenone and 2,2-methylenebis[4-(1,1,3,3-tetramethylbutyl)-6-[(2H-benzotriazole-2-yl)phenol]] can be also added. By adding them, light resistance of the norbornene ring-opened (co)polymer of the invention can be improved. Moreover, additives such as lubricants can be also added for the purpose of improving processability.

Process for Preparing Norbornene Ring-opened (Co)Polymer

In the process for preparing a norbornene ring-opened (co)polymer of the invention, a norbornene monomer (Im) represented by the following formula (Im) is subjected to ring-opening (co)polymerization singly or, if necessary, together with a norbornene monomer (IIm) represented by the following formula (IIm).

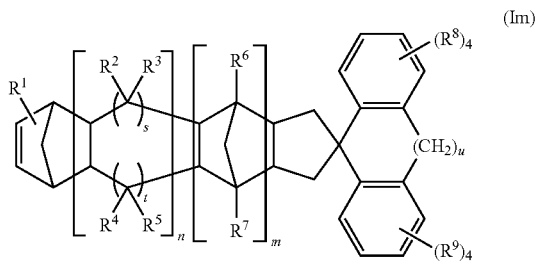

(Im)

In the formula (Im), m and n are each independently an integer of 0 to 2,
$R^1$, $R^2$, $R^3$, $R^4$, $R^5$, $R^6$, $R^7$, $R^8$ and $R^9$ are each independently an atom or a group selected from the group consisting of a hydrogen atom, a halogen atom, a substituted or unsubstituted hydrocarbon group of 1 to 30 carbon atoms which may have a linkage containing an oxygen atom, a nitrogen atom, a sulfur atom or a silicon atom, and a polar group, and
s, t and u are each independently an integer of 0 to 3.

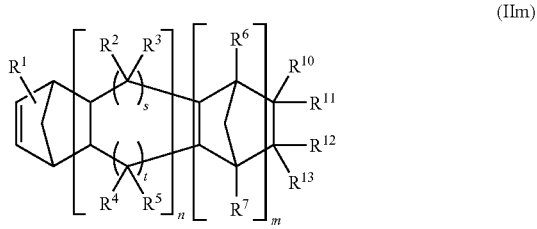

(IIm)

In the formula (IIm), m and n are each independently an integer of 0 to 2,
$R^1$, $R^2$, $R^3$, $R^4$, $R^5$, $R^6$ and $R^7$ are each independently an atom or a group selected from the group consisting of a hydrogen atom, a halogen atom, a substituted or unsubstituted hydrocarbon group of 1 to 30 carbon atoms which may have a linkage containing an oxygen atom, a nitrogen atom, a sulfur atom or a silicon atom, and a polar group, $R^{10}$, $R^{11}$, $R^{12}$ and $R^{13}$ are each independently an atom or a group selected from the group consisting of a hydrogen atom, a halogen atom, a substituted or unsubstituted hydrocarbon group of 1 to 30 carbon atoms which may have a linkage containing an oxygen atom, a nitrogen atom, a sulfur atom or a silicon atom, and a polar group, they may be bonded to each other to form a monocyclic or polycyclic group which may have a hetero atom, and $R^{10}$ and $R^{11}$, or $R^{12}$ and $R^{13}$ may be united to form a divalent hydrocarbon group, and
s and t are each independently an integer of 0 to 3.

In the norbornene monomer (Im), m, n, X, $R^1$ to $R^9$, s, t and u are the same as those in the aforesaid structural units (I), and the norbornene monomer (Im) is the same as the aforesaid norbornene derivative of the invention. In the norbornene monomer (IIm), m, n, X, $R^1$ to $R^7$, $R^{10}$ to $R^{13}$, s and t are the same as those in the aforesaid structural units (II).

The composition of a stereoisomer of the norbornene monomer (Im) is not specifically restricted, and it has only to be properly selected according to the desired properties. The norbornene monomer (Im) imparts "negative birefringence properties" to a (co)polymer, so that by properly copolymerizing the norbornene monomer (Im) with the norbornene monomer (IIm) that imparts "positive birefringence properties" to a (co)polymer, it becomes possible to obtain a (co) polymer which dose not substantially exhibit birefringence. The "positive or negative of birefringence properties" referred to herein is determined from a change of refractive index occurring when a film is monoaxially stretched, and properties that the refractive index in the stretching direction becomes larger than the refractive index in the direction perpendicular to the stretching direction is defined as "positive birefringence properties" and properties that the refractive index in the stretching direction becomes smaller than the refractive index in the direction perpendicular to the stretching direction is defined as "negative birefringence properties".

Regarding the substituents on the aromatic ring, by introducing functional groups having great polarization (e.g., ester group, alkoxy group), the wavelength dependence of birefringence can be made greater.

As the norbornene monomer (Im), the aforesaid norbornene derivative of the invention represented by the formula (Im) is available.

In the process for preparing a norbornene ring-opened (co)polymer of the invention, the norbornene monomers (Im) can be used singly or in combination of two or more kinds.

In the process for preparing a norbornene ring-opened (co)polymer of the invention, of the norbornene monomers (Im), a monomer of the formula (Im) wherein m=0, n=0 and u=0 is preferably employed. Such a monomer is preferable because it can be relatively easily synthesized and is easily obtainable, and besides, the resulting ring-opened (co)polymer and its hydrogenation product have both of heat resistance and toughness.

Examples of the norbornene monomers (IIm) represented by the formula (IIm), which can be optionally copolymerized with the norbornene monomer (Im) in the preparation process of the invention, include the following compounds:
 bicyclo[2.2.1]hept-2-ene,
 tricyclo[4.3.0.1$^{2,5}$]-3-decene,
 tricyclo[4.4.0.1$^{2,5}$]-3-undecene,
 tetracyclo[4.4.0.1$^{2,5}$.1$^{7,10}$]-3-dodecene,
 pentacyclo[6.5.1.1$^{3,6}$.0$^{2,7}$.0$^{9,13}$]-4-pentadecene,
 pentacyclo[7.4.0.1$^{2,5}$.1$^{9,12}$.0$^{8,13}$]-3-pentadecene,
 5-methylbicyclo[2.2.1]hept-2-ene,
 5-ethylbicyclo[2.2.1]hept-2-ene,
 5-methoxycarbonylbicyclo[2.2.1]hept-2-ene, 5-methyl-5-methoxycarbonylbicyclo[2.2.1]hept-2-ene,
5-cyanobicyclo[2.2.1]hept-2-ene,
8-methoxycarbonyltetracyclo[4.4.0.1$^{2,5}$.1$^{7,10}$]-3-dodecene,
8-ethoxycarbonyltetracyclo[4.4.0.1$^{2,5}$.1$^{7,10}$]-3-dodecene,
8-n-propoxycarbonyltetracyclo[4.4.0.1$^{2,5}$.1$^{7,10}$]-3-dodecene,
8-isopropoxycarbonyltetracyclo[4.4.0.1$^{2,5}$.1$^{7,10}$]-3-dodecene,
8-n-butoxycarbonyltetracyclo[4.4.0.1$^{2,5}$.1$^{7,10}$]-3-dodecene,
8-phenoxycarbonyltetracyclo[4.4.0.1$^{2,5}$.1$^{7,10}$]-3-dodecene,
8-(1-naphthoxy)carbonyltetracyclo[4.4.0.1$^{2,5}$.1$^{7,10}$]-3-dodecene,
8-(2-naphthoxy)carbonyltetracyclo[4.4.0.1$^{2,5}$.1$^{7,10}$]-3-dodecene,
8-(4-phenylphenoxy)carbonyltetracyclo[4.4.0.1$^{2,5}$.1$^{7,10}$]-3-dodecene,
8-methyl-8-methoxycarbonyltetracyclo[4.4.0.1$^{2,5}$.1$^{7,10}$]-3-dodecene,
8-methyl-8-ethoxycarbonyltetracyclo[4.4.0.1$^{2,5}$.1$^{7,10}$]-3-dodecene,
8-methyl-8-n-propoxycarbonyltetracyclo[4.4.0.1$^{2,5}$.1$^{7,10}$]-3-dodecene,
8-methyl-8-isopropoxycarbonyltetracyclo[4.4.0.1$^{2,5}$.1$^{7,10}$]-3-dodecene,
8-methyl-8-n-butoxycarbonyltetracyclo[4.4.0.1$^{2,5}$.1$^{7,10}$]-3-dodecene,
8-methyl-8-phenoxycarbonyltetracyclo[4.4.0.1$^{2,5}$.1$^{7,10}$]-3-dodecene,
8-methyl-8-(1-naphthoxy)carbonyltetracyclo[4.4.0.1$^{2,5}$.1$^{7,10}$]-3-dodecene,
8-methyl-8-(2-naphthoxy)carbonyltetracyclo[4.4.0.1$^{2,5}$.1$^{7,10}$]-3-dodecene,
8-methyl-8-(4-phenylphenoxy)carbonyltetracyclo[4.4.0.1$^{2,5}$.1$^{7,10}$]-3-dodecene,
pentacyclo[8.4.0.1$^{2,5}$.1$^{9,12}$.0$^{8,13}$]-3-hexadecene,
heptacyclo[8.7.0.1$^{3,6}$.1$^{10,17}$.0$^{12,15}$.0$^{2,7}$.0$^{11,16}$]-4-eicosene,
heptacyclo[8.8.0.1$^{4,7}$.1$^{11,18}$.0$^{13,16}$.0$^{3,8}$.0$^{12,17}$]-5-heneicosene,
5-ethylidenebicyclo[2.2.1]hept-2-ene,
8-ethylidenetetracyclo[4.4.0.1$^{2,5}$.1$^{7,10}$]-3-dodecene,
5-phenylbicyclo[2.2.1]hept-2-ene,
5-phenyl-5-methylbicyclo[2.2.1]hept-2-ene,
8-phenyltetracyclo[4.4.0.1$^{2,5}$.1$^{7,10}$]-3-dodecene,
5-n-butylbicyclo[2.2.1]hept-2-ene,
5-n-hexylbicyclo[2.2.1]hept-2-ene,
5-cyclohexylbicyclo[2.2.1]hept-2-ene,
5-(2-cyclohexenyl)bicyclo[2.2.1]hept-2-ene,
5-n-octylbicyclo[2.2.1]hept-2-ene,
5-n-decylbicyclo[2.2.1]hept-2-ene,
5-isopropylbicyclo[2.2.1]hept-2-ene,
5-(1-naphthyl)bicyclo[2.2.1]hept-2-ene,
5-(2-naphthyl)bicyclo[2.2.1]hept-2-ene,
5-(2-naphthyl)-5-methylbicyclo[2.2.1]hept-2-ene,
5-(4-biphenyl)bicyclo[2.2.1]hept-2-ene,
5-(4-biphenyl)-5-methylbicyclo[2.2.1]hept-2-ene,
5-aminomethylbicyclo[2.2.1]hept-2-ene,
5-trimethoxysilylbicyclo[2.2.1]hept-2-ene,
5-triethoxysilylbicyclo[2.2.1]hept-2-ene,
5-tri-n-propoxysilylbicyclo[2.2.1]hept-2-ene,
5-tri-n-butoxysilylbicyclo[2.2.1]hept-2-ene,
5-chloromethylbicyclo[2.2.1]hept-2-ene,
5-hydroxymethylbicyclo[2.2.1]hept-2-ene,
5-cyclohexenylbicyclo[2.2.1]hept-2-ene,
5-fluorobicyclo[2.2.1]hept-2-ene,
5-fluoromethylbicyclo[2.2.1]hept-2-ene,
5-trifluoromethylbicyclo[2.2.1]hept-2-ene,
5,5-difluorobicyclo[2.2.1]hept-2-ene,
5,6-difluorobicyclo[2.2.1]hept-2-ene,
5,5-bis(trifluoromethyl)bicyclo[2.2.1]hept-2-ene,
5,6-bis(trifluoromethyl)bicyclo[2.2.1]hept-2-ene,
5-methyl-5-trifluoromethylbicyclo[2.2.1]hept-2-ene,
5,5,6-trifluorobicyclo[2.2.1]hept-2-ene,
5,5,6,6-tetrafluorobicyclo[2.2.1]hept-2-ene,
8-fluorotetracyclo[4.4.0.1$^{2,5}$.1$^{7,10}$]-3-dodecene,
8-fluoromethyltetracyclo[4.4.0.1$^{2,5}$.1$^{7,10}$]-3-dodecene,
8-trifluoromethyltetracyclo[4.4.0.1$^{2,5}$.1$^{7,10}$]-3-dodecene, and
8,8-difluorotetracyclo[4.4.0.1$^{2,5}$.1$^{7,11}$]-3-dodecene.

The above norbornene monomers (IIm) may be used singly or as a mixture of two or more kinds, in combination with the norbornene monomer (Im).

Of the norbornene monomers (IIm), norbornene monomers wherein at least one of $R^{10}$, $R^{11}$, $R^{12}$ and $R^{13}$ in the formula (IIm) is a carboxylic ester group represented by —(CH$_2$)$_p$COOR$^{14}$ (R$^{14}$ is a hydrocarbon group of 1 to 20 carbon atoms and p is an integer of 0 to 10) are preferable from the viewpoint of a balance among heat resistance of the resulting copolymer, solubility thereof and adhesion or bonding thereof to other materials, and 8-methyl-8-methoxycarbonyltetracyclo[4.4.0.1$^{2,5}$.1$^{7,10}$]-3-dodecene is more preferable from the viewpoint of ease of preparation process. Examples of the hydrocarbon groups of 1 to 20 carbon atoms indicated by R$^{14}$ include alkyl groups, such as methyl, ethyl and propyl, aryl groups, such as phenyl, and aralkyl groups, such as benzyl. Of these, preferable are methyl, ethyl and phenyl, and particularly preferable is methyl. p is an integer of 0 to 10, particularly preferably 0.

In the present invention, the molar ratio of the norbornene monomer (Im) to the norbornene monomer (IIm) is in the range of usually 100/0 to 2/98, preferably 100/0 to 5/95, more preferably 100/0 to 10/90.

If the molar ratio of the norbornene monomer (Im) to the norbornene monomer (IIm) is lower than 2/98, specific wavelength dependence of birefringence (as the wavelength becomes longer, birefringence becomes greater) and properties of low birefringence, which are effects of the invention, cannot be obtained occasionally.

In the present invention, in addition to the norbornene monomer (Im) and the norbornene monomer (IIm), other copolymerizable monomers can be used within limits not detrimental to the effects of the invention. Also in this case, the norbornene monomer (Im) is preferably used in an amount of not less than 2% by mol based on all the monomers. Examples of the copolymerizable monomers other than the norbornene monomer (Im) and the norbornene monomer (IIm) include cycloolefins, such as cyclobutene, cyclopentene, cyclooctene and cyclododecene; and non-conjugated polyenes, such as 1,4-cyclooctadiene, dicylopentadiene and cyclododecatriene. In the present invention, ring-opening polymerization of the norbornene monomer (Im) and the like may be carried out in the presence of polybutadiene, polyisoprene, styrene-butadiene, an ethylene/non-conjugated diene polymer or a non-hydrogenation product of a ring-opened (co)polymer of a norbornene monomer The polymerization conditions in the process for preparing a norbornene ring-opened (co)polymer of the invention are further described below.

Ring-Opening Polymerization Catalyst

As a ring-opening polymerization catalyst for use in the invention, a catalyst described in "Olefin Metathesis and Metathesis Polymerization" (K. J. IVIN, J. C. MOL, Academic Press, 1997) is preferably employed.

Such a catalyst is, for example, a metathesis polymerization catalyst consisting of a combination of (a) at least one compound selected from compounds of W, Mo, Re, V and Ti and (b) at least one compound selected from compounds containing Li, Na, K, Mg, Ca, Zn, Cd, Hg, B, Al, Si, Sn, Pb and the like and having at least one of said element-carbon bonds or one of said element-hydrogen bonds. This catalyst may be a catalyst to which the later-described additives have been added in order to enhance the catalytic activity. As another catalyst, a metathesis catalyst (d) which uses no co-catalyst and comprises a Group 4 to Group 8 transition metal-carbene complex or a metallacyclobutene complex is employable.

Typical examples of the compounds of W, Mo, Re, V and Ti which are suitable as the components (a) include compounds described in Japanese Patent Laid-Open Publication No. 240517/1989, such as $WCl_6$, $MoCl_5$, $ReOCl_3$ and $TiCl_4$.

Examples of the components (b) include compounds described in Japanese Patent Laid-Open Publication No. 240517/1989, such as n-$C_4H_9Li$, $(C_2H_5)_3Al$, $(C_2H_5)_2AlCl_1$, $(C_2H_5)_{1.5}AlCl_{1.5}$, $(C_2H_5)AlCl_2$, methylalumoxane and LiH.

Typical examples of the components (c) which are preferably used as additives include alcohols, aldehydes, ketones and amines. Further, compounds described in Japanese Patent Laid-Open Publication No. 240517/1989 are also employable.

Typical examples of the catalysts (d) include W(=N—2,6-$C_6H_3iPr_2$) (=CHtBu) $(OtBu)_2$, Mo(=N-2,6-$C_6H_3iPr_2$) (=CHtBu) $(OtBu)_2$, Ru(=CHCH=$CPh_2$) $(PPh_3)_2Cl_2$ and Ru(=CHPh) $(PC_6H_{11})_2Cl_2$.

The metathesis catalyst is used in such an amount that the molar ratio between the component (a) and the specific monomers (total of the norbornene monomer (Im) and the norbornene monomer (IIm)) (component (a):specific monomers) becomes usually 1:500 to 1:500000, preferably 1:1000 to 1:100000. The ratio between the component (a) and the component (b) ((a):(b) is desirably in the range of 1:1 to 1:50, preferably 1:2 to 1:30, in terms of a metal atom ratio. The molar ratio between the component (c) and the component (a) ((c):(a)) is desirably in the range of 0.005:1 to 15:1, preferably 0.05:1 to 7:1. The catalyst (d) is desirably used in such an amount that the molar ratio between the component (d) and the specific monomers (total of the norbornene monomer (Im) and the norbornene monomer (IIm)) (component (d):specific monomers) becomes usually 1:50 to 1:50000, preferably 1:100 to 1:10000.

Molecular Weight Modifier

Control of a molecular weight of a ring-opened polymer can be carried out by properly selecting polymerization temperature, type of a catalyst and type of a solvent, but in the present invention, it is preferable to control the molecular weight by allowing a molecular weight modifier to coexist in the reaction system. Preferred examples of the molecular weight modifiers include α-olefins, such as ethylene, propylene, 1-butene, 1-pentene, 1-hexene, 1-heptene, 1-octene, 1-nonene and 1-decene, and styrene. Of these, 1-butene and 1-hexene are particularly preferable. These molecular weight modifiers can be used singly or in combination of two or more kinds. The molecular weight modifier is used in an amount of 0.001 to 0.6 mol, preferably 0.02 to 0.5 mol, based on 1 mol of the specific monomers (total of the norbornene monomers (Im) and (IIm)) used in the ring-opening (co)polymerization reaction.

Ring-Opening Polymerization Reaction Solvent

Examples of solvents used in the ring-opening polymerization reaction, namely, solvents used for dissolving the norbornene monomers, the metathesis catalyst and the molecular weight modifier, include alkanes, such as pentane, hexane, heptane, octane, nonane and decane; cycloalkanes, such as cyclohexane, cycloheptane, cyclooctane, decalin and norbornane; aromatic hydrocarbons, such as benzene, toluene, xylene, ethylbenzene and cumene; halogenated alkanes, such as chlorobutane, bromohexane, methylene chloride, dichloroethane, hexamethylene dibromide, chlorobenzene, chloroform and tetrachloroethylene; compounds, such as aryl; saturated carboxylic esters, such as ethyl acetate, n-butyl acetate, isobutyl acetate, methyl propionate and dimethoxyethane; and ethers, such as dibutyl ether, tetrahydrofuran and dimethoxyethane. These solvents can be used singly or as a mixture. Of these, aromatic hydrocarbons are preferable in the present invention.

The solvent is used in such an amount that the ratio between the solvent and the specific monomers (solvent:specific monomers, by weight) becomes usually 1:1 to 10:1, preferably 1:1 to 5:1.

Hydrogenation

In the present invention, the norbornene ring-opened (co) polymer may be prepared by only the ring-opening polymerization, but it is preferable to further perform hydrogenation of the ring-opened (co)polymer obtained by the ring-opening polymerization. In the norbornene ring-opened (co)polymer obtained by only the ring-opening polymerization, each X in the structural units (I) represented by the formula (I) and in the structural units (II) represented by the formula (II) is an olefinic unsaturated group represented by the formula —CH=CH—. This ring-opened (co)polymer of the invention can be used as it is, but from the viewpoint of heat stability, preferable is a hydrogenation product wherein the olefinic unsaturated group is hydrogenated to convert X into a group represented by —$CH_2$—$CH_2$—. The hydrogenation product referred to in the present invention, however, is a product wherein the olefinic unsaturated group is hydrogenated but the aromatic ring on the side chain based on the norbornene monomer is not substantially hydrogenated.

The degree of hydrogenation is desired to be not less than 90% by mol, preferably not less than 95% by mol, more preferably not less than 97% by mol, of the total of X in the structural units (I) and the structural units (II). As the degree of hydrogenation is increased, coloring or deterioration due to heat can be inhibited more effectively, so that higher degree of hydrogenation is preferable.

In the preparation process of the invention, the hydrogenation reaction needs to be carried out under such conditions that the aromatic rings on the side chain based on the norbornene monomer (Im) and the optionally used norbornene monomer (IIm) are not substantially hydrogenated. Therefore, the hydrogenation reaction is desirably carried out by adding a hydrogenation catalyst to a solution of the ring-opened polymer and allowing the catalyst to act thereon at a pressure of usually atmospheric pressure to 300 μm, preferably 3 to 200 atm, and a temperature of usually 0 to 200° C., preferably 20 to 180° C.

As the hydrogenation catalyst, a catalyst usually used for hydrogenation reaction of olefinic compounds is employable, and any of publicly known heterogeneous catalysts and homogeneous catalysts is employable. Examples of the heterogeneous catalysts include solid catalysts in which noble metal catalyst materials, such as palladium, platinum, nickel, rhodium and ruthenium, are supported on carriers, such as carbon, silica, alumina and titania. Examples of the homogeneous catalysts include nickel naphthenate/triethylaluminum, nickel acetylacetonate/triethylaluminum, cobalt octenate/n-butyllithium, titanocene dichloride/diethylaluminum monochloride, rhodium acetate, chlorotris(triphenylphosphine)rhodium, dichlorotris(triphenylphosphine)ruthenium, chlorohydrocarbonyltris(triphenylphosphine)ruthenium and dichlorocarbonyltris(triphenylphosphine)ruthenium. The catalyst may be in the form of a powder or particles.

In order that the aromatic rings on the side chain based on the norbornene monomer (Im) and other monomers are not substantially hydrogenated, the amount of the hydrogenation catalyst added needs to be controlled, and it is desirable to use the catalyst usually in such an amount that the "ring-opened polymer:hydrogenation catalyst ratio by weight" becomes $1:1\times10^{-6}$ to 1:2.

In the preparation process of the invention, the norbornene ring-opened (co)polymer of the invention or its hydrogenation product desirably has a logarithmic viscosity ($\eta_{inh}$), as measured by an Ubbelohde viscometer, of usually 0.2 to 5.0, preferably 0.3 to 4.0, more preferably 0.35 to 3.0. Further, the norbornene ring-opened (co)polymer or its hydrogenation product desirably has a number-average molecular weight (Mn), as measured by gel permeation chromatography (GPC, tetrahydrofuran solvent, in term of polystyrene), of usually 1000 to 500000, preferably 2000 to 300000, more preferably 5000 to 300000, and a weight-average molecular weight (Mw), as measured by the gel permeation chromatography, of usually 5000 to 2000000, preferably 10000 to 1000000, more preferably 10000 to 500000. If the logarithmic viscosity ($\eta_{inh}$) is less than 0.2 and if the number-average molecular weight (Mn) is less than 1000 or the weight-average molecular weight (Mw) is less than 5000, strength of a molded product obtained from the resulting norbornene ring-opened (co)polymer is sometimes markedly lowered. If the logarithmic viscosity ($\eta_{inh}$) is more than 5.0 and if the number-average molecular weight (Mn) is more than 500000 or the weight-average molecular weight (Mw) is more than 2000000, melt viscosity or solution viscosity of the norbornene ring-opened (co)polymer or its hydrogenation product becomes too high and it sometimes becomes difficult to obtain a desired molded article.

The ring-opened (co)polymer or its hydrogenation product obtained by the process for preparing a norbornene ring-opened (co)polymer of the invention is the aforesaid norbornene ring-opened (co)polymer of the invention, has excellent transparency, heat resistance and low-water absorption properties, and exhibits specific wavelength dependence of birefringence.

To the ring-opened (co)polymer or its hydrogenation product obtained by the preparation process of the invention, various additives, such as the aforesaid antioxidants, ultraviolet light absorbers and lubricants, may be added when needed, and the ring-opened (co)polymer or its hydrogenation product can be favorably applied particularly to uses in the fields of optical parts and electric or electronic materials. Examples of such use applications include optical discs, photomagnetic discs, optical lenses (Fθ lens, pickup lens, laser printer lens, camera lens, etc.), spectacle lenses, optical films (display film, retardation film, polarizing film, transparent conductive film, wave plate, anti-reflection film, optical pickup film, etc.), optical sheets, optical fibers, light guide plates, light diffusion plates, optical cards, optical mirrors, and IC/LSI/LED sealing materials.

According to the present invention, by properly controlling composition, a novel norbornene derivative that is useful as a precursor monomer for preparing a cycloolefin polymer exhibiting excellent transparency, heat resistance and low-water absorption properties and having been freely controlled in the birefringence and the wavelength dispersion properties can be provided.

In the norbornene derivative of the invention, an aromatic ring is fixed in the direction perpendicular to a cyclo ring by means of a spiro bond, and hence, a polymer obtained by the use of the norbornene derivative of the invention can be freely controlled in the birefringence and the wavelength dispersion properties by properly controlling the amount of the norbornene derivative. Such a norbornene derivative of the invention is very useful as an optical resin precursor, and a polymer obtained by the use of the norbornene derivative can be applied to optical materials requiring optical design of extremely high precision, such as optical discs, photomagnetic discs, optical lenses (Fθ lens, pickup lens, laser printer lens, camera lens, etc.), spectacle lenses, optical films/sheets (display film, retardation film, polarizing film, polarizing plate protective film, diffusion film, anti-reflection film, liquid crystal substrate, EL substrate, substrate for electronic paper, touch panel substrate, PDP front panel, etc.), substrates for transparent conductive films, optical fibers, light guide plates, optical cards, optical mirrors, and IC/LSI/LEI sealing materials.

According to the present invention, further, a norbornene ring-opened (co)polymer having excellent transparency and heat resistance, exhibiting high solubility in organic solvents and having specific birefringence and wavelength dependence, and a process for preparing the ring-opened (co)polymer can be provided. In the present invention, by properly controlling composition of structural unit 3 for a norbornene ring-opened (co)polymer and substituents of the structural units, a norbornene ring-opened (co)polymer having excellent transparency and heat resistance, exhibiting high solubility in organic solvents and having freely controlled desired birefringence and wavelength dependence, and a process for preparing the ring-opened (co)polymer can be provided.

The norbornene ring-opened (co)polymer of the invention can be used by properly molding it into a desired shape, and can be favorably used for molded articles such as optical parts and electric or electronic materials.

EXAMPLES

The present invention is further described with reference to the following examples, but it should be construed that the invention is, in no way limited to those examples. Unless otherwise noted, "%" and "part(s)" are those on the basis of weight.

In the following examples and comparative examples, various measurements and evaluation were carried out in the following manner.

Glass Transition Temperature (Tg)

Glass transition temperature was measured at a heating rate of 20° C./min in a stream of nitrogen using a differential scanning calorimeter manufactured by Seiko Instruments Inc.

Molecular Weight and Molecular Weight Distribution

Weight-average molecular weight (Mw) in terms of polystyrene and molecular weight distribution (Mw/Mn) (Mn: number-average molecular weight) were determined by gel permeation chromatography (GPC) using HLC-8020 manufactured by TOSOH CORPORATION and using a tetrahydrofuran (THF) solvent.

Evaluation of Phase Difference and Birefringence

Retardation (Re) defined by the following formula was measured by a retardation measuring device (KOBRA21DH, manufactured by Oji Scientific Instruments).

$$Re=(nx-ny)\times d$$

nx: refractive index in the stretching direction ny: refractive index in the direction perpendicular to the stretching direction d: film thickness (nm)

A stretched film obtained in the following manner was used as a sample. A toluene or methylene chloride solution of a resin was cast on a glass plate and dried to prepare a film having a thickness of 100 μm and a solvent residue of not more than 0.2%. The resulting cast film was monoaxially stretched to 1.3 times at a temperature of Tg of resin+10° C., to obtain a sample film.

Example 1

Synthesis of spiro[fluorene-9,8'-tricyclo[4.3.0.1$^{2,5}$][3]decene] (exo form)

Into a 1000 ml flask equipped with a dropping funnel, 30.96 g (0.2008 mol) of 5-norbornene-2exo-3exo-dimethanol was weighed, and the system was purged with nitrogen. Then, 250 ml (3.0973 mol) of pyridine was added and sufficiently stirred by a stirrer to give a solution. Then, the reaction system was kept at 0° C. in an ice cooling bath, and to the reaction system, 84.21 g (0.4412 mol) of p-toluenesulfonyl chloride having been previously dissolved in 130 ml of dehydrated THF (tetrahydrofuran) was dropwise added slowly with sufficiently stirring. After the dropwise addition was completed, stirring was continued for 8 hours in the ice cooling bath to perform reaction. After the reaction was completed, the reaction mixture was washed three times with a 0.12N hydrochloric acid aqueous solution, then three times with a saturated sodium hydrogencarbonate aqueous solution and then three times with distilled water, followed by drying over sodium sulfate. Thereafter, the solvent was removed by heating under reduced pressure and the resulting crystals were recrystallized by the use of a n-hexane/ethyl acetate mixed solvent to obtain 44.50 g of 2exo,3exo-bis-(toluene-4-sulfonyloxy)-5-norbornene as white crystals.

Separately, 18.76 g (0.1128 mol) of fluorene was weighed into a 1000 ml flask equipped with a dropping funnel, and the system was purged with nitrogen. Then, 100 ml of dehydrated THF was added and sufficiently stirred by a stirrer to give a solution. Then, 141 ml of a hexane solution of n-butyllithium (1.6 mol/l) was dropwise added slowly with keeping the temperature of the reaction system at −78° C. in a dry ice bath. After the dropwise addition was completed, stirring was continued for 1 hour with keeping the reaction system at −78° C. To the reaction solution, a solution obtained by previously dissolving 26.10 g (0.0564 mol) of the above-obtained 2,3-bis-(toluene-4-sulfonyloxy)-5-norbornene in 500 ml of dehydrated THF was dropwise added slowly with keeping the temperature of the reaction system at −78° C. After the dropwise addition was completed, stirring was continued for 1 hour in the dry ice bath. Thereafter, the cooling bath was removed, and stirring was continued until the temperature of the reaction system completely returned to room temperature (about 3 hours). To the reaction solution was added a salt solution to quench the solution. Then, the reaction solution was washed three times with distilled water and dried over sodium sulfate. Thereafter, the solvent was removed by heating under reduced pressure, and the resulting crystals were recrystallized by the use of methanol to obtain 10.09 g of light yellow crystals.

Figure 2:
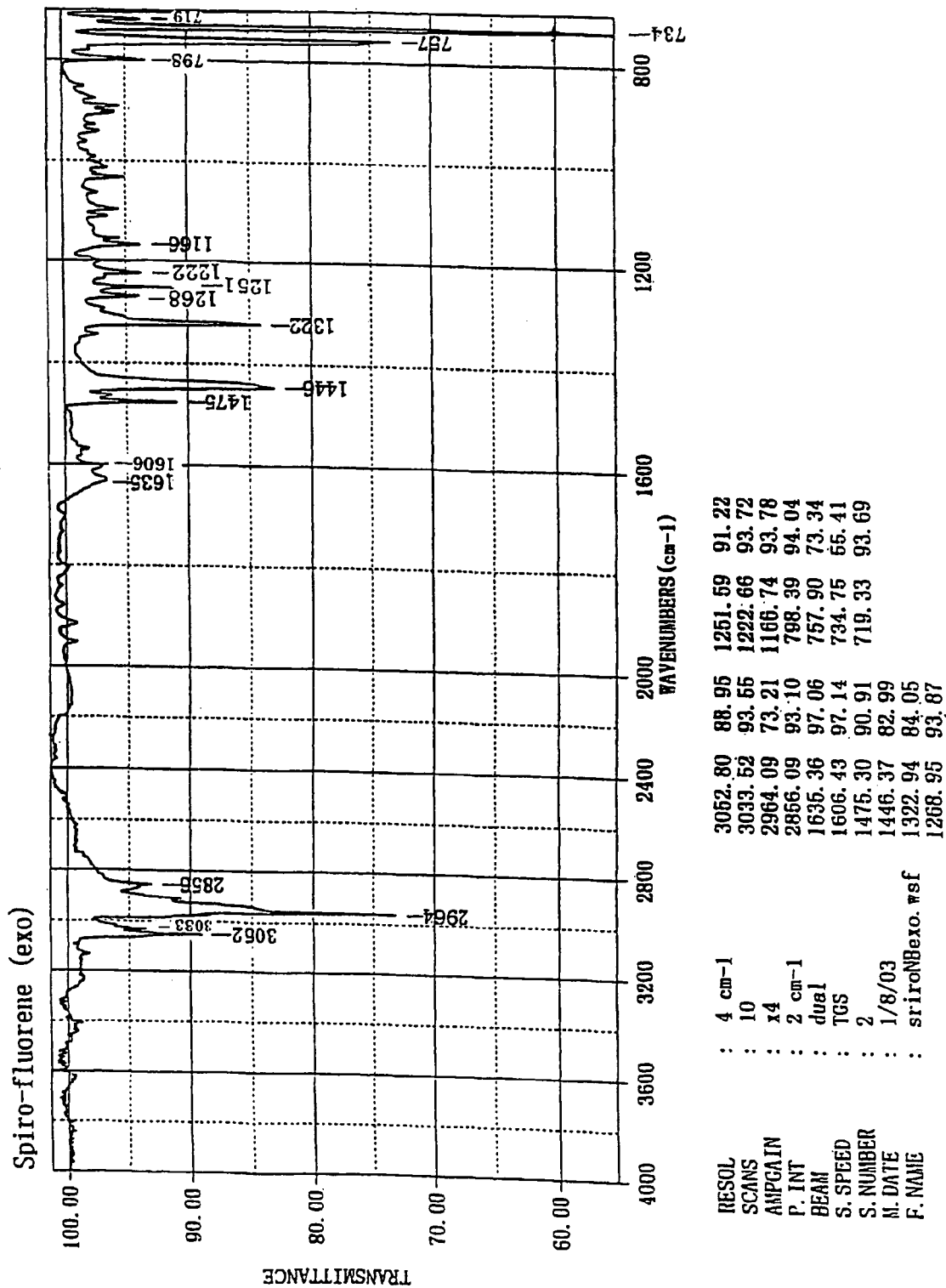
FIG. 2 shows an infrared absorption (IR) spectrum of a norbornene derivative obtained in Example 1.

A $^1$H-NMR spectrum of the resulting crystals is shown in FIG. 1, and an infrared absorption (IR) spectrum thereof is shown in FIG. 2.

From the results, the resulting crystals were confirmed to be spiro[fluorene-9,8'-tricyclo[4.3.0.1$^{2,5}$][3]decene] (exo form).

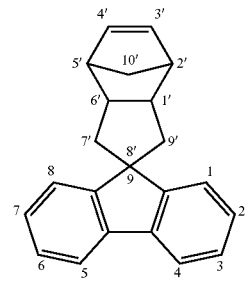

Example 2

Synthesis of spiro[fluorene-9,8'-tricyclo[4.3.0.1$^{2,5}$][3]decene] (endo form)

Into a 1000 ml flask equipped with a dropping funnel, 50.0 g (0.3242 mol) of 5-norbornene-2endo-3endo-dimethanol was weighed, and the system was purged with nitrogen. Then, 225 ml (2.7876 mol) of pyridine was added and sufficiently stirred by a stirrer to give a solution. Then, the reaction system was kept at 0° C. in an ice cooling bath, and to the reaction system, 136.0 g (0.7133 mol) of p-toluenesulfonyl chloride having been previously dissolved in 180 ml of dehydrated THF (tetrahydrofuran) was dropwise added slowly with sufficiently stirring. After the dropwise addition was completed, stirring was continued for 8 hours in the ice cooling bath to perform reaction. After the reaction was completed, the reaction mixture was washed three times with a 0.12N hydrochloric acid aqueous solution, then three times with a saturated sodium hydrogencarbonate aqueous solution and then three times with distilled water, followed by drying over sodium sulfate. Thereafter, the solvent was removed by heating under reduced pressure, and the resulting crystals were recrystallized by the use of a n-hexane/ethyl acetate mixed solvent to obtain 21.60 g of 2endo,3endo-bis-(toluene-4-sulfonyloxy)-5-norbornene as white crystals.

Separately, 15.52 g (0.0934 mol) of fluorene was weighed into a 1000 ml flask equipped with a dropping funnel, and the system was purged with nitrogen. Then, 165 ml of dehydrated THF was added and sufficiently stirred by a stirrer to give a solution. Then, 117 ml of a hexane solution of n-butyllithium (1.6 mol/l) was dropwise added slowly with keeping the temperature of the reaction system at −78° C. in a cry ice bath. After the dropwise addition was completed, stirring was continued for 1 hour with keeping the reaction system at −78° C. To the reaction solution, a solution obtained by previously dissolving 21.60 g of the above-obtained 2endo,3endo-bis-(toluene-4-sulfonyloxy)-5-norbornene in 500 ml of dehydrated THF was dropwise added slowly with keeping the temperature of the reaction system at −78° C. After the dropwise addition was completed, stirring was continued for 1 hour in the dry ice bath. Thereafter, the cooling bath was removed, and stirring was continued until the temperature of the reaction system completely returned to room temperature (about 3 hours). To the reaction solution was added a salt solution to quench the solution. Then, the reaction solution was washed three times with distilled water and dried over sodium sulfate. Thereafter, the solvent was removed by heating under reduced pressure, and the resulting crystals were recrystallized by the use of methanol to obtain 5.68 g of light yellow crystals.

Figure 3:
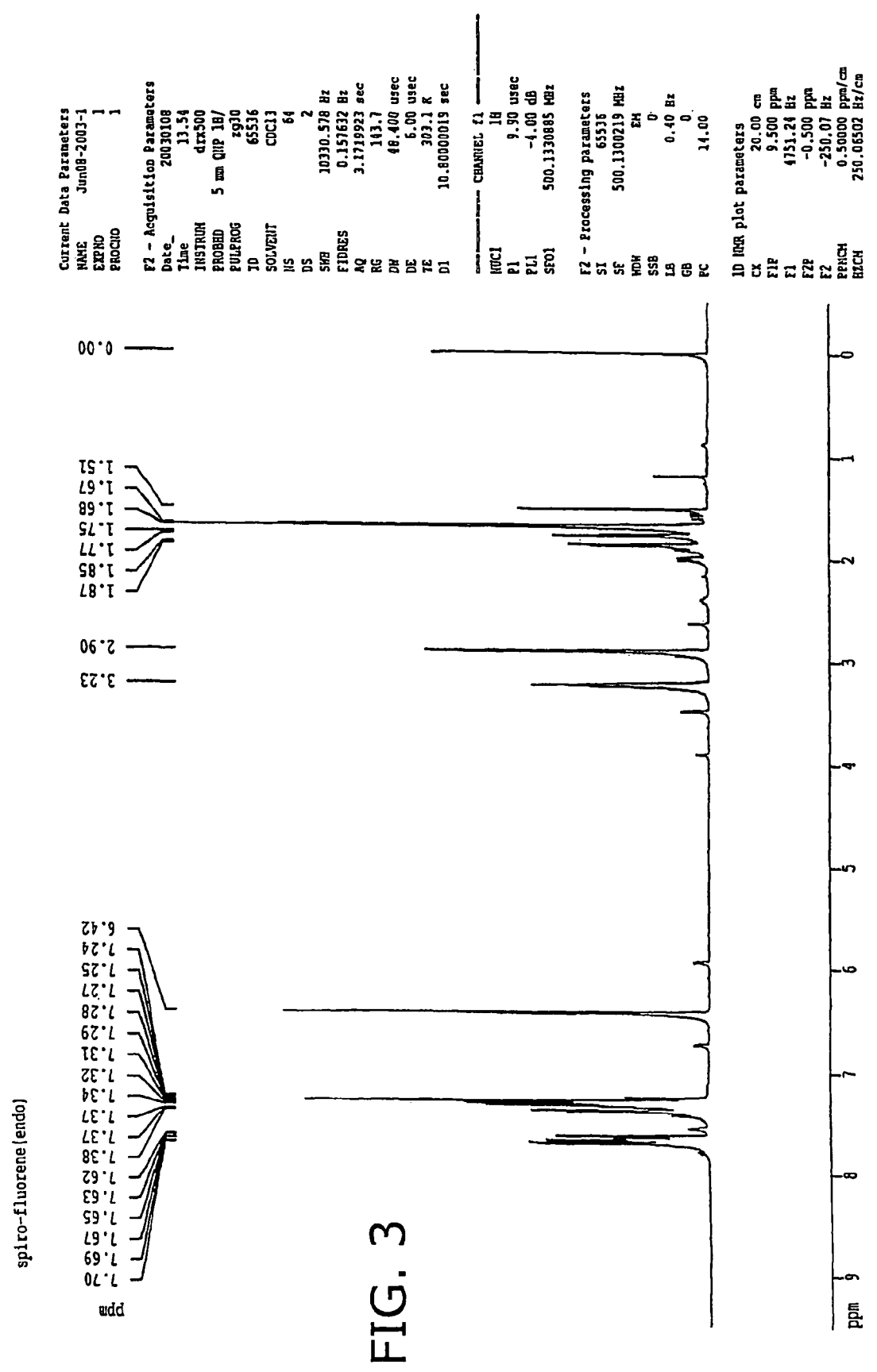
Figure 4:
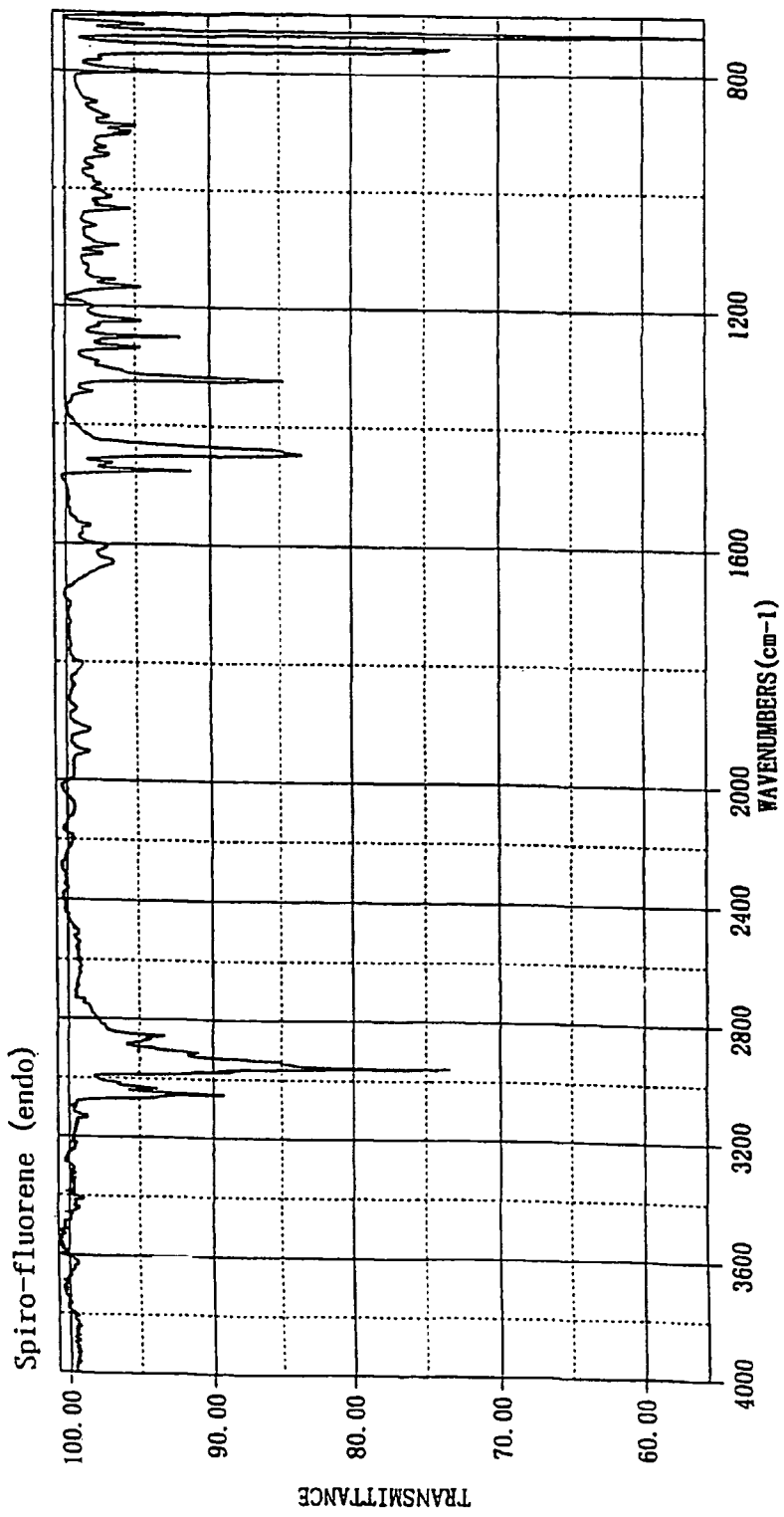
FIG. 4 shows an infrared absorption (IR) spectrum of a norbornene derivative obtained in Example 2.

A $^1$H-NMR spectrum of the resulting crystals is shown in FIG. 3, and an infrared absorption (IR) spectrum thereof is shown in FIG. 4.

From the results, the resulting crystals were confirmed to be spiro[fluorene-9,8'-tricyclo[4.3.0.1$^{2,5}$][3]decene] (endo form).

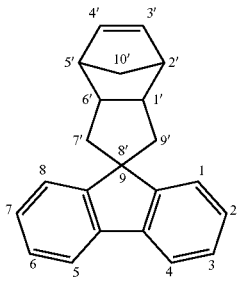

Example 3

In a reaction vessel purged with nitrogen, 3.67 g of the spiro[fluorene-9,8'-tricyclo[4.3.0.1$^{2,5}$][3]decene] (exo form) obtained in Example 1, 3.0 g of 8-methoxycarbonyl-8-methyltetracyclo[4.4.0.1$^{2,5}$.1$^{7,10}$]-3-dodecene represented by the following formula, 0.20 g of 1-hexene as a molecular weight modifier and 13.4 g of toluene were placed, and they were heated to 80° C.

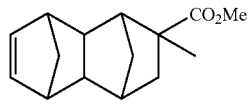

To the mixture, 0.068 ml of a toluene solution of triethylaluminum (0.6 mol/l) and 0.21 ml of a toluene solution of methanol modified WCl$_6$ (0.025 mol/l) were added, and they were reacted at 80° C. for 0.5 hour to obtain a ring-opened copolymer solution. The resulting ring-opened copolymer had a weight-average molecular weight (Mw) of 28.0×10$^4$ and a molecular weight distribution (Mw/Mn) of 6.08.

Figure 5:
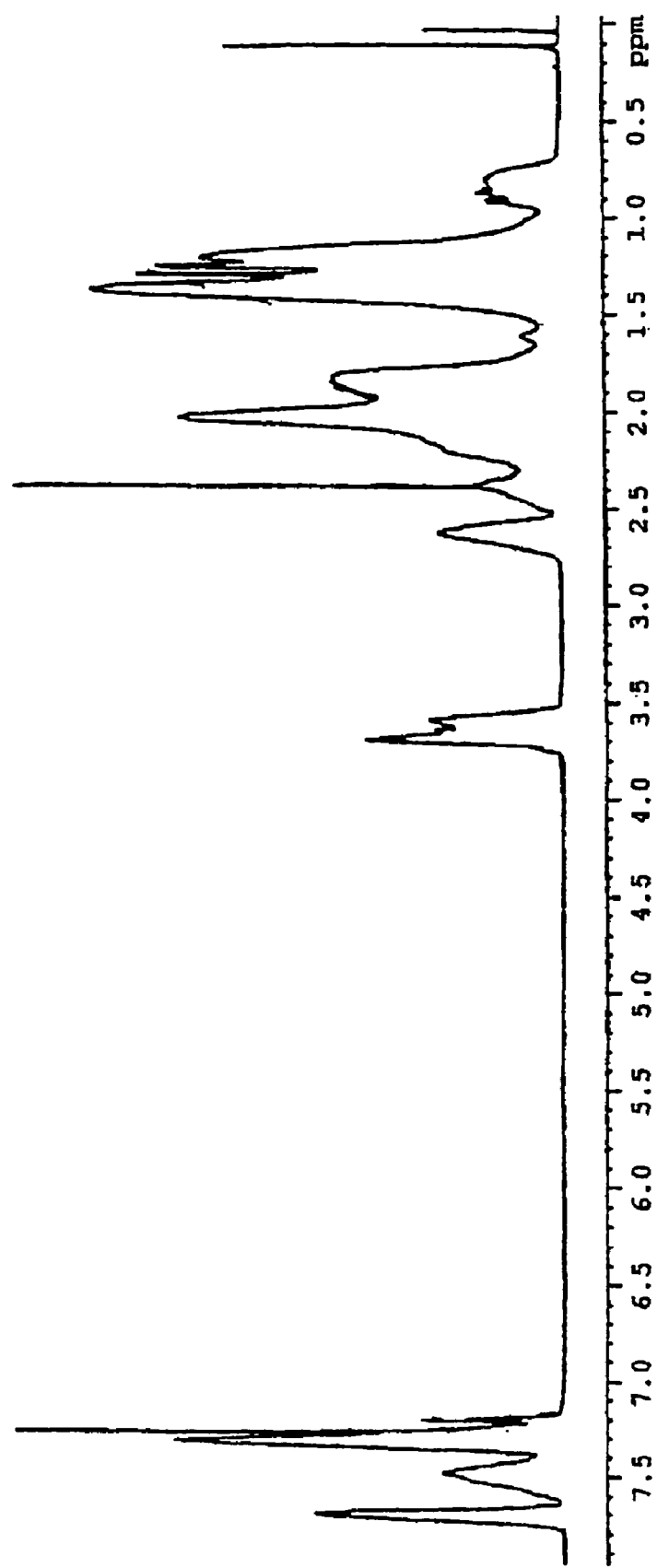
FIG. 5 shows a $^1$H-NMR spectrum of a ring-opened polymer hydrogenation product obtained in Example 3.
Figure 6:
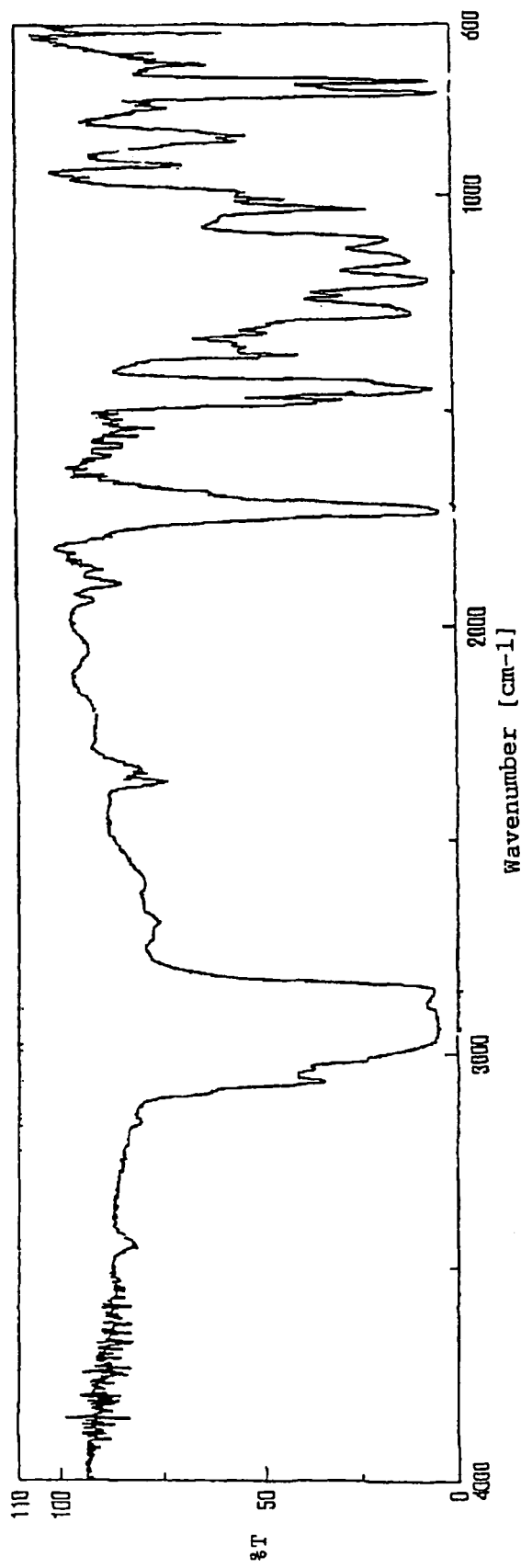
FIG. 6 shows an infrared absorption (IR) spectrum of a ring-opened polymer hydrogenation product obtained in Example 3.

Subsequently, the resulting ring-opened copolymer solution was placed in an autoclave, and thereto was further added 300 g of toluene. Then, RuHCl(CO) [P(C$_6$H$_5$)]$_3$ as a hydrogenation catalyst was added in an amount of 2500 ppm based on the amount of the monomers used, and reaction was performed at a hydrogen gas pressure of 9 to 10 MPa and a temperature of 160 to 165° C. for 4 hours. After the reaction was completed, a reaction product was precipitated in a large amount of a methanol solution to obtain a hydrogenation product. The resulting hydrogenation product of the ring-opened copolymer had a weight-average molecular weight (Mw) of 26.9×10$^4$, a molecular weight distribution (Mw/Mn) of 4.37, an inherent viscosity ($\eta_{inh}$) of 1.07 and a glass transition temperature (Tg) of 188.8° C. A $^1$H-NMR spectrum of the resulting hydrogenation product of the ring-opened copolymer is shown in FIG. 5, and an infrared absorption (IR) spectrum thereof is shown in FIG. 6. As a result of NMR measurements, a degree of hydrogenation of the hydrogenation product was not less than 97.0% and an aromatic ring residue thereof was 100%.

From the resulting hydrogenation product of the ring-opened copolymer, a colorless transparent cast film having a thickness of 100 μm and a solvent residue of not more than 0.2% was obtained by a solvent cast method. Then, the resulting film was monoaxially stretched to 1.3 times at 199° C. to obtain a stretched film as a sample for evaluation.

The resulting stretched film was measured on a retardation at a wavelength of 550 nm (Re550), and from the film thickness (d (nm)), birefringence (nx-ny) was determined. In order to evaluate wavelength dependence of birefringence, ratios of retardations at wavelengths of 481 nm and 748 nm (Re481 and Re748) to a retardation at a wavelength of 550 nm (Re550) were determined. The results are all set forth in Table 1.

Example 4

In a reaction vessel purged with nitrogen, 1.53 g of the spiro[fluorene-9,8'-tricyclo[4.3.0.1$^{2,5}$][3]decene] (endo form) obtained in Example 2, 5.0 g of 8-methoxycarbonyl-8-methyltetracyclo[4.4.0.1$^{2,5}$.1$^{7,10}$]-3-dodecene, 0.20 g of 1-hexene as a molecular weight modifier and 12.5 g of toluene were placed, and they were heated to 80° C. To the mixture, 0.068 ml of a toluene solution of triethylaluminum (0.6 mol/l) and 0.21 ml of a toluene solution of methanol modified WCl$_6$ (0.025 mol/l) were added, and they were reacted at 80° C. for 0.5 hour to obtain a ring-opened copolymer solution. The resulting ring-opened copolymer had a weight-average molecular weight (Mw) of 37.1×10$^4$ and a molecular weight distribution (Mw/Mn) of 7.98.

Figure 7:
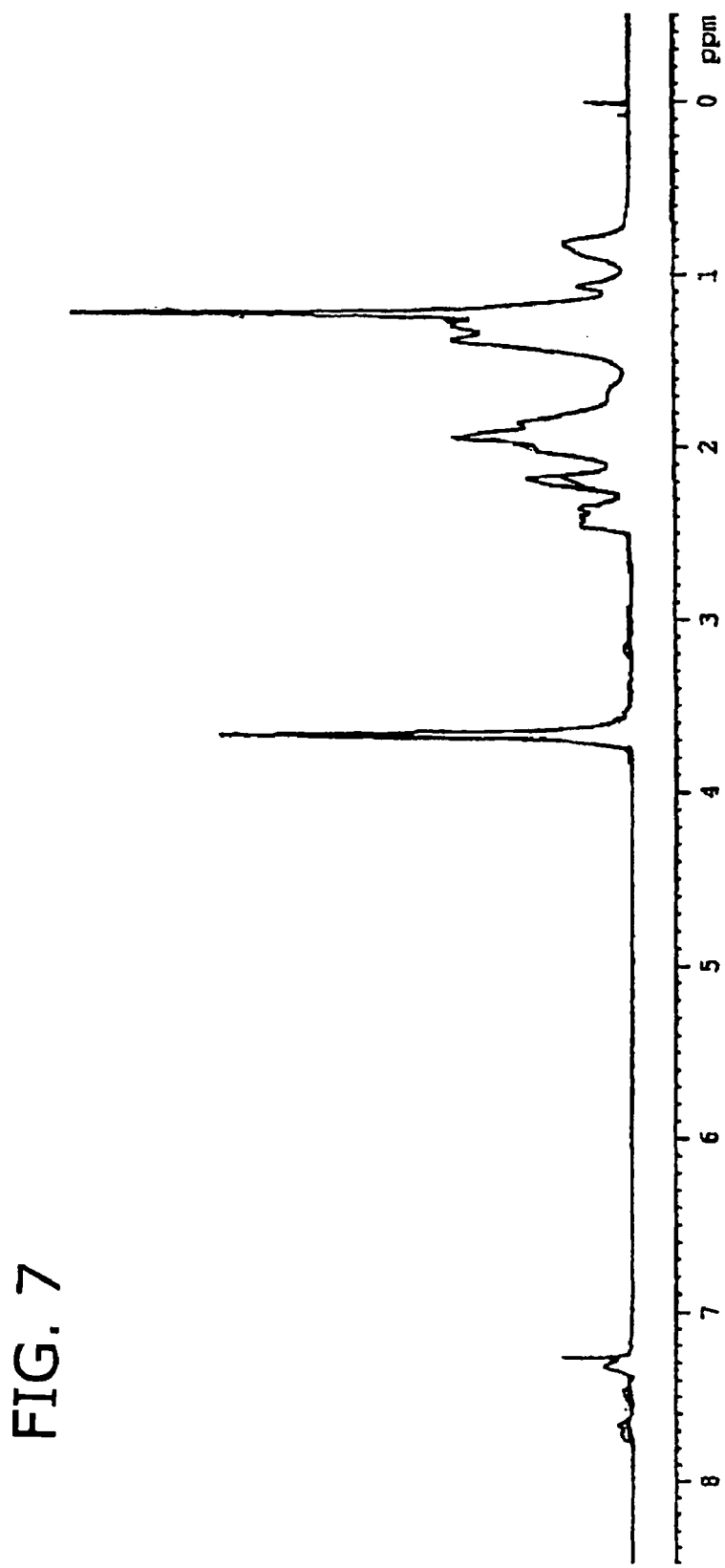
FIG. 7 shows a $^1$H-NMR spectrum of a ring-opened polymer hydrogenation product obtained in Example 4.
Figure 8:
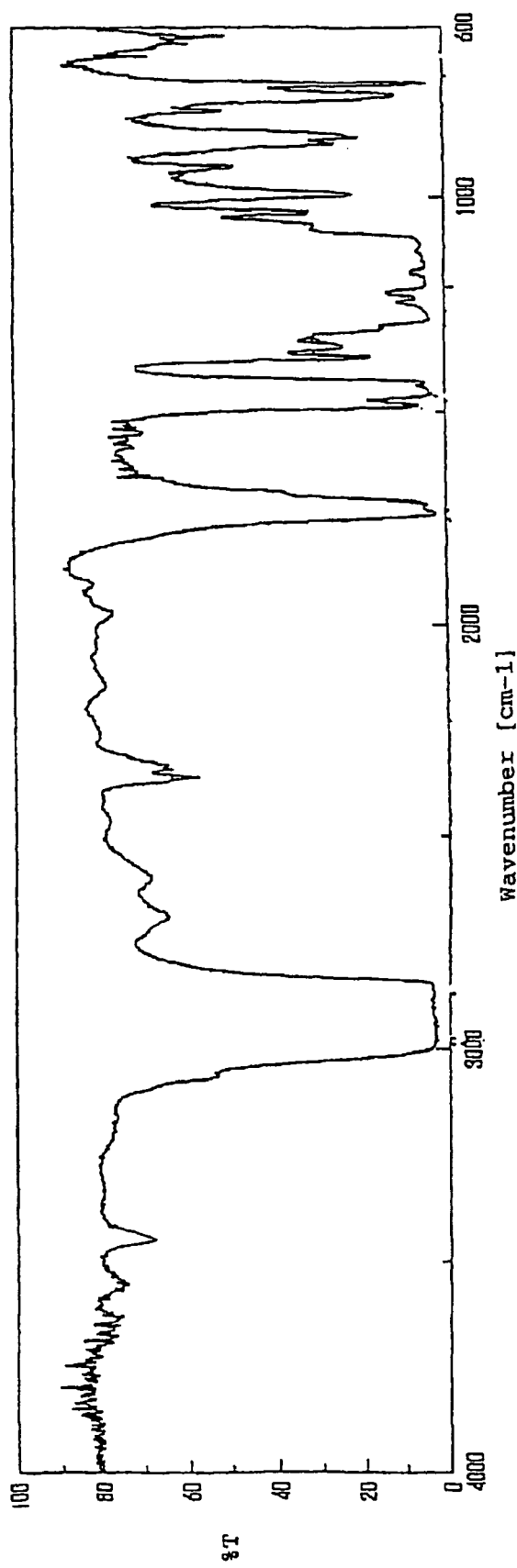
FIG. 8 shows an infrared absorption (IR) spectrum of a ring-opened polymer hydrogenation product obtained in Example 4.

Subsequently, hydrogenation reaction was carried out in the same manner as in Example 3 to obtain a hydrogenation product. The resulting hydrogenation product of the ring-opened copolymer had a weight-average molecular weight (Mw) of 37.2×10$^4$, a molecular weight distribution (Mw/Mn) of 6.23, an inherent viscosity ($\eta_{inh}$) of 1.28 and a glass transition temperature (Tg) of 185.3° C. A $^1$H-NMR spectrum of the resulting hydrogenation product of the ring-opened copolymer is shown in FIG. 7, and an infrared absorption (IR), spectrum thereof is shown in FIG. 8. As a result of NMR measurements, a degree of hydrogenation of the hydrogenation product was not less than 97.0% and an aromatic ring residue thereof was 100%.

From the resulting hydrogenation product of the ring-opened copolymer, a colorless transparent cast film having a thickness of 100 μm and a solvent residue of not more than 0.2% was obtained by a solvent cast method. Then, the resulting film was monoaxially stretched to 1.3 times at 195° C. to obtain a stretched film as a sample for evaluation.

The resulting stretched film was measured on a retardation at a wavelength of 550 nm (Re550), and from the film thickness (d (nm)), birefringence (nx-ny) was determined. In order to evaluate wavelength dependence of birefringence, ratios of retardations at wavelengths of 481 nm and 748 nm (Re481 and Re748) to a retardation at a wavelength of 550 nm (Re550) were determined. The results are all set forth in Table 1.

Comparative Example 1

In a reaction vessel purged with nitrogen, 50 g of 8-methoxycarbonyl-8-methyltetracyclo[4.4.0.1$^{2,5}$.1$^{7,10}$]-3-dodecene, 3.6 g of 1-hexene as a molecular weight modifier and 100 g of toluene were placed, and they were heated to 80° C. To the mixture, 0.09 ml of a toluene solution of triethylaluminum (0.6 mol/l) and 0.29 ml of a toluene solution of methanol modified WCl$_6$ (0.025 mol/l) were added, and they were reacted at 80° C. for 3 hours to obtain a polymer. Subsequently, hydrogenation reaction was carried out in the same manner as in Example 3 to obtain a hydrogenation product. The resulting hydrogenation product of the ring-opened polymer had a glass transition temperature (Tg) of 167° C., a weight-average molecular weight (Mw) of 5.6×10$^4$ and a molecular weight distribution (Mw/Mn) of 3.20. As a result of NMR measurements, a degree of hydrogenation of the hydrogenation product was not less than 97.0%.

From the hydrogenation product of the ring-opened polymer, a colorless transparent cast film having a thickness of 100 μm and a solvent residue of not more than 0.2% was obtained by a solvent cast method. Then, the resulting film was monoaxially stretched to 1.3 times at 177° C. to obtain a stretched film as a sample for evaluation.

The resulting stretched film was measured on a retardation at a wavelength of 550 nm (Re550), and from the film thickness (d (nm)), birefringence (nx−ny) was determined. In order to evaluate wavelength dependence of birefringence, ratios of retardations at wavelengths of 481 nm and 748 nm (Re481 and Re748) to a retardation at a wavelength of 550 nm (Re550) were determined. The results are all set forth in Table 1.

TABLE 1

|   | Birefringence ($\times 10^{-4}$) | Re481/ Re550 | Re748/ Re550 | Stretch ratio (times) | Glass transition temperature (° C.) |
| --- | --- | --- | --- | --- | --- |
| Ex. 3 | −20.7 | 1.14 | 0.90 | 1.3 | 188.8 |
| Ex. 4 | 17.0 | 0.97 | 1.02 | 1.3 | 185.3 |
| Comp. Ex. 1 | 18.6 | 1.01 | 1.00 | 1.3 | 167.0 |

From the comparison between Example 3 and Example 4, it has been clarified that positive or negative and magnitude of birefringence can be controlled by controlling a copolymerization compositional ratio of the norbornene monomer (Im) of the invention.

With regard to the wavelength dependence of birefringence, the dependence on the measuring wavelength was small in Comparative Example 1, while the wavelength dependence was great in Examples 3 and 4. Further, in Example 3, such wavelength dependence observed in usual polymers that the birefringence becomes smaller as the wavelength becomes longer was shown, while in Example 4, such wavelength dependence reverse to the usual dependence that the birefringence becomes greater as the wavelength becomes longer was shown. That is to say, it has been clarified that the wavelength dependence of birefringence can be also controlled by controlling a copolymerization compositional ratio of the norbornene monomer (Im) of the invention.

The invention claimed is:

1. A norbornene derivative represented by formula (Im):

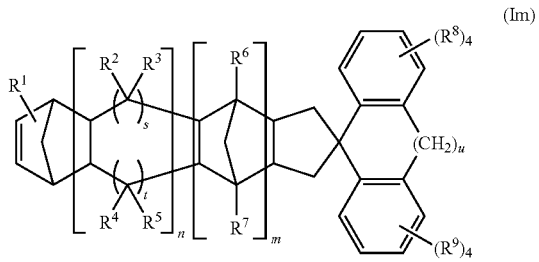

(Im)

wherein
$R^1$, $R^2$, $R^3$, $R^4$, $R^5$, $R^6$, $R^7$, $R^8$ and $R^9$ are each independently an atom or a group selected from the group consisting of a hydrogen atom, a halogen atom, a substituted hydrocarbon group of 1 to 30 carbon atoms, a substituted hydrocarbon groups of 1 to 30 carbon atoms having a linkage containing an oxygen atom, a nitrogen atom, a sulfur atom, or a silicon atom, an unsubstituted hydrocarbon group of 1 to 30 carbon atoms, an unsubstituted hydrocarbon group of 1 to 30 carbon atoms having a linkage containing an oxygen atom, a nitrogen atom, a sulfur atom or a silicon atom, and a polar group, s, t and u are each independently an integer of 0 to 3, and m and n are each independently an integer of 0 to 2.

2. The norbornene derivative as claimed in claim 1, wherein n is 0 and m is 0 or 1.

3. The norbornene derivative as claimed in claim 1, wherein u is 0 or 1.

4. The norbornene derivative as claimed in claim 1, wherein n is 1 or 2, s and t are each 1, and u is 0 or 1.

5. The norbornene derivative as claimed in claim 1, wherein 3 or more of $R^8$ and 3 or more of $R^9$ are each a hydrogen atom.

6. The norbornene derivative as claimed in claim 2, wherein u is 0 or 1.

7. The norbornene derivative as claimed in claim 1, wherein said linkage is at least one selected from the group consisting of a carbonyl group, a carbonyloxy group, a sulfonyl group, a sulfonyl ester group, a ether bond, a thioether bond, an imino group, an amide bond, and a siloxane bond.

8. The norbornene derivative as claimed in claim 1, wherein said polar group is at least one selected from the group consisting of a hydroxyl group, an alkoxy group of 1 to 10 carbon atoms, a carbonyloxy group, an alkoxycarbonyl group, an aryloxycarbonyl group, a cyano group, an amide group, an imide group, a triorganosiloxy group, a triorganosilyl group, an amino group, an acyl group, an alkoxysilyl group, a sulfonyl group and a carboxyl group.

9. The norbornene derivative as claimed in claim 1, wherein said polar group is at least one selected from the group consisting of a methoxy group, an ethoxy group, an acetoxy group, a propionyloxy group, a benzoyloxy group, a methoxycarbonyl group, an ethoxycarbonyl group, a phenoxycarbonyl group, a naphthyloxycarbonyl group, a fluorenyloxycarbonyl group, a biphenylyloxycarbonyl group, a trimethylsiloxy group, an triethylsiloxy group, a trimethylsilyl group, a triethylsilyl group, a primary amino group, a trimethoxysilyl group, and a triethoxysilyl group.

10. The norbornene derivative as claimed in claim 1, which is at least one selected from the group consisting of
spiro[fluorene-9,8'-tricyclo[4.3.0.1$^{2,5}$][3]decene];
spiro[2,7-difluorofluorene-9,8'-tricyclo[4.3.0.1$^{2,5}$][3]decene];
spiro[2,7-dichlorofluorene-9,8'-tricyclo[4.3.0.1$^{2,5}$][3]decene];
spiro[2,7-dibromofluorene-9,8'-tricyclo[4.3.0.1$^{2,5}$][3]decene];
spiro[2-methoxyfluorene-9,8'-tricyclo[4.3.0.1$^{2,5}$][3]decene];
spiro[2-ethoxyfluorene-9,8'-tricyclo[4.3.0.1$^{2,5}$][3]decene];
spiro[2-phenoxyfluorene-9,8'-tricyclo[4.3.0.1$^{2,5}$][3]decene];
spiro[2,7-dimethoxyfluorene-9,8'-tricyclo[4.3.0.1$^{2,5}$][3]decene];
spiro[2,7-diethoxyfluorene-9,8'-tricyclo[4.3.0.1$^{2,5}$][3]decene];
spiro[2,7-diphenoxyfluorene-9,8'-tricyclo[4.3.0.1$^{2,5}$][3]decene];
spiro[3,6-dimethoxyfluorene-9,8'-tricyclo[4.3.0.1$^{2,5}$][3]decene];
spiro[fluorene-9,8'-[2]methyltricyclo[4.3.0.1$^{2,5}$][3]decene]; and
spiro[fluorene-9,8'-[10]methyltricyclo[4.3.0.1$^{2,5}$][3]decene].

11. The norbornene derivative as claimed in claim 1, wherein m is 0, n is 0, u is 0, and 3 or more of $R^8$ and 3 or more of $R^9$ are each a hydrogen atom.

* * * * *